US 11,497,548 B2

United States Patent
Gittard et al.

(10) Patent No.: US 11,497,548 B2
(45) Date of Patent: Nov. 15, 2022

(54) BIPOLAR SPHINCTEROTOME

(71) Applicant: Cook Medical Technologies LLC, Bloomington, IN (US)

(72) Inventors: Shaun D. Gittard, Winston-Salem, NC (US); Gregory J Hardy, Winston-Salem, NC (US); Michelle D. Martinez, Winston-Salem, NC (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 57 days.

(21) Appl. No.: 17/075,173

(22) Filed: Oct. 20, 2020

(65) Prior Publication Data
US 2021/0100610 A1   Apr. 8, 2021

Related U.S. Application Data

(60) Division of application No. 15/339,534, filed on Oct. 31, 2016, now Pat. No. 10,806,509, which is a
(Continued)

(51) Int. Cl.
*A61B 18/14* (2006.01)
*A61B 18/16* (2006.01)
(Continued)

(52) U.S. Cl.
CPC ........ *A61B 18/1482* (2013.01); *A61B 18/149* (2013.01); *A61B 18/16* (2013.01);
(Continued)

(58) Field of Classification Search
CPC .. A61B 2018/1407; A61B 2018/00077; A61B 2018/165; A61B 90/90;
(Continued)

(56) References Cited

U.S. PATENT DOCUMENTS

| 1,983,669 A | 12/1934 | Kimble |
| 2,056,377 A | 10/1936 | Wappler |

(Continued)

FOREIGN PATENT DOCUMENTS

| CN | 102164557 A | 8/2011 |
| DE | 2426781 | 12/1975 |

(Continued)

OTHER PUBLICATIONS

International Search Report and Written Opinion for corresponding application No. PCT/US2013/077800 dated Jun. 11, 2014.
(Continued)

*Primary Examiner* — Paul D Kim
(74) *Attorney, Agent, or Firm* — Crowell & Moring LLC

(57) ABSTRACT

A conductive coating may be adhered to a structure comprising a hydrophobic and/or adhesion-resistant surface. The conductive coating may have a polymer backbone with conductive particles suspended in the backbone. In some embodiments, the conductive coating may be applied directly to the surface. In other embodiments, the conductive coating may be indirectly applied by first applying a primer adhesive to the outer surface, and then applying the conductive coating over the primer adhesive. An example structure may be a catheter of an endoscopic medical device, such as a bipolar sphincterotome, where the conductive coating functions as a return electrode.

7 Claims, 16 Drawing Sheets

Related U.S. Application Data continuation-in-part of application No. 14/139,214, filed on Dec. 23, 2013, now Pat. No. 9,844,407.

(60) Provisional application No. 61/746,162, filed on Dec. 27, 2012.

(51) Int. Cl.

| | |
|---|---|
| *B05D 3/00* | (2006.01) |
| *B05D 7/00* | (2006.01) |
| *B05D 3/12* | (2006.01) |
| *A61B 17/00* | (2006.01) |
| *A61B 18/00* | (2006.01) |
| *A61B 90/90* | (2016.01) |
| *A61M 25/00* | (2006.01) |

(52) U.S. Cl.
CPC .............. *B05D 3/002* (2013.01); *B05D 3/12* (2013.01); *B05D 7/544* (2013.01); *A61B 90/90* (2016.02); *A61B 2017/003* (2013.01); *A61B 2018/00077* (2013.01); *A61B 2018/00148* (2013.01); *A61B 2018/00166* (2013.01); *A61B 2018/00553* (2013.01); *A61B 2018/00601* (2013.01); *A61B 2018/1407* (2013.01); *A61B 2018/1475* (2013.01); *A61B 2018/162* (2013.01); *A61B 2018/165* (2013.01); *A61M 25/0045* (2013.01)

(58) Field of Classification Search
CPC ... A61B 18/1482; A61B 18/149; A61B 18/16; A61B 2017/003; A61B 2018/00148; A61B 2018/00166; A61B 2018/00553; A61B 2018/00601; A61B 2018/162; A61B 2018/1475; B05D 3/12; B05D 3/002; B05D 7/544; A61M 25/0045
See application file for complete search history.

(56) References Cited

U.S. PATENT DOCUMENTS

| | | | |
|---|---|---|---|
| 4,476,862 A | | 10/1984 | Pao |
| 4,823,791 A | | 4/1989 | D'Amelio et al. |
| 5,007,908 A | | 4/1991 | Rydell |
| 5,035,696 A | * | 7/1991 | Rydell .................. A61B 18/14 606/47 |
| 5,201,732 A | | 4/1993 | Parins et al. |
| 5,254,121 A | | 10/1993 | Manevitz et al. |
| 5,462,545 A | | 10/1995 | Wang et al. |
| 5,480,399 A | | 1/1996 | Hebborn |
| 5,562,720 A | | 10/1996 | Stem |
| 5,925,045 A | | 7/1999 | Reimels et al. |
| 5,944,715 A | | 8/1999 | Goble et al. |
| 5,991,650 A | | 11/1999 | Swanson et al. |
| 6,027,501 A | | 2/2000 | Goble et al. |
| 6,032,061 A | | 2/2000 | Koblish |
| 6,071,281 A | | 6/2000 | Burnside et al. |
| 6,097,976 A | * | 8/2000 | Yang ..................... A61L 29/085 606/41 |
| 6,114,021 A | | 9/2000 | Pankratz |
| 6,440,128 B1 | | 8/2002 | Edwards et al. |
| 6,514,248 B1 | | 2/2003 | Eggers et al. |
| 6,533,963 B1 | * | 3/2003 | Schleifstein ............. C08K 9/02 252/514 |
| 6,712,817 B1 | | 3/2004 | Goto et al. |
| 6,884,535 B2 | | 4/2005 | Saito |
| 7,879,030 B2 | | 2/2011 | Paul et al. |
| 8,142,431 B2 | | 3/2012 | Ducharme |
| 9,311,831 B2 | | 4/2016 | Henshue |
| 2002/0095152 A1 | | 7/2002 | Ciarrocca et al. |
| 2003/0049437 A1 | | 3/2003 | Devaney |
| 2003/0114849 A1 | | 6/2003 | Ryan |
| 2003/0181900 A1 | | 9/2003 | Long |
| 2004/0015162 A1 | | 1/2004 | McGaffigan |
| 2005/0119654 A1 | | 6/2005 | Swanson et al. |
| 2005/0203441 A1 | | 9/2005 | Voegele |
| 2007/0027448 A1 | | 2/2007 | Paul et al. |
| 2007/0106292 A1 | | 5/2007 | Kaplan et al. |
| 2008/0161774 A1 | | 7/2008 | Hastings |
| 2009/0318746 A1 | | 12/2009 | Thurmond, II et al. |
| 2010/0057077 A1 | | 3/2010 | Ducharme |
| 2010/0082026 A1 | | 4/2010 | Curtis |
| 2010/0114093 A1 | | 5/2010 | Mahapatra |
| 2012/0071870 A1 | | 3/2012 | Salahieh |
| 2012/0089141 A1 | | 4/2012 | Lee et al. |
| 2012/0123411 A1 | | 5/2012 | Ibrahim et al. |
| 2012/0310265 A1 | | 12/2012 | Martinez |
| 2015/0374434 A1 | | 12/2015 | Gayzik et al. |

FOREIGN PATENT DOCUMENTS

| | | |
|---|---|---|
| DE | 3315303 | 11/1984 |
| EP | 0440 385 A2 | 8/1991 |
| EP | 0 959 786 | 12/1999 |
| JP | 7-51288 A | 2/1995 |
| JP | 2008-529610 A | 8/2008 |
| WO | WO 97/48345 | 12/1997 |
| WO | WO 2006/084316 A1 | 8/2006 |
| WO | WO 2014/105950 A1 | 7/2014 |
| WO | WO 2016/022430 A1 | 2/2016 |

OTHER PUBLICATIONS

International Search Report and Written Opinion for corresponding application No. PCT/US2014/068272, dated Jun. 11, 2014.
Invitation to Pay Additional Fee for corresponding application No. PCT/US2013/077800 dated Mar. 25, 2014.
Invitation to Pay Additional Fee for corresponding application No. PCT/US2014/068272 dated Feb. 18, 2015.
Jerome H. Siegel, M.D. et al, "Bipolar Versus Monopolar Sphincterotomy: A Prospective Trial", The American Journal of Gastroenterology, vol. 89, No. 10, 1994, pp. 1827-1830.
Robert D. Tucker, M.D. et al., "Bipolar Electrosurgical Sphincterotomy", The American Society for Gastrointestinal Endoscopy, vol. 38, No. 2. 1992, pp. 113-117.
Office Action in corresponding U.S. Appl. No. 14/139,214, dated Feb. 16, 2016, 17 pages.
Office Action in corresponding U.S. Appl. No. 14/139,214, dated Jun. 9, 2016, 16 pages.
Office Action, and English language translation thereof, in corresponding Japanese Application No. 2015-550765, dated Jun. 15, 2016, 9 pages.
Office Action in corresponding U.S. Appl. No. 14/560,563, dated Feb. 7, 2017, 15 pages.
International Search Report and Written Opinion in International Application No. PCT/US2017/058687, dated Feb. 13, 2018, 14 pages.
Chinese Office Action with translation in Chinese Patent Application No. 201710342992X dated Apr. 28, 2019 (11 pages).

\* cited by examiner

BIPOLAR SPHINCTEROTOME

CROSS-REFERENCE TO RELATED APPLICATION

The present application is a divisional of U.S. Non-Provisional application Ser. No. 15/339,534, filed Oct. 31, 2016, now U.S. Pat. No. 10,806,509, which is a continuation-in-part of U.S. Non-Provisional application Ser. No. 14/139,214, filed Dec. 23, 2013 (now U.S. Pat. No. 9,844,407 issued Dec. 19, 2017), which claims the benefit of U.S. Provisional Application No. 61/746,162, filed Dec. 27, 2012. The contents of U.S. Non-Provisional application Ser. No. 15/339,534 and Ser. No. 14/139,214 and U.S. Provisional Application No. 61/746,162 are hereby incorporated by reference in their entirety.

TECHNICAL FIELD

The present invention relates generally to medical devices, and more particularly to bipolar sphincterotomes.

BACKGROUND

A sphincterotome is a medical device that is used to perform a sphincterotomy, which involves cutting a sphincter muscle, such as the sphincter of Oddi. The sphincter muscle may need to be cut to relieve its constrictive nature and allow one or more medical devices through the muscle. For example, problems occurring in the biliary tree, such as the formation of bile duct stones or papillary stenosis, may be treated using medical devices that are delivered into the biliary tree. In order to access the biliary tree, the medical devices may pass through the sphincter of Oddi. To facilitate passage of the medical devices through the sphincter of Oddi, the sphincter muscle may be cut using a sphincterotome.

A sphincterotome may generally include an elongate tubular member, such as a catheter, and a cutting wire that is used to cut the sphincter muscle. The cutting wire may extend through a lumen of the catheter, except at a distal portion of the catheter, where the cutting wire may project from and be exposed outside of the catheter. The exposed portion, which may be referred to as a cutting edge, may be used to cut the sphincter muscle.

A sphincterotomy generally involves a two-part process: cannulation of the biliary tree and cutting the sphincter muscle by sending electric current through the cutting wire (i.e, electrosurgery). Cannulation of the biliary tree may include inserting the distal portion of the catheter into the papilla and using the distal portion and the cutting edge to lift an upper portion (i.e., the roof) of the papilla. The roof of the papilla may be lifted by proximally pulling the cutting wire taut, causing the distal portion of the tubular member to bow and form an arc. After cannulation, the electric current may be provided to the cutting edge to cut the sphincter muscle.

BRIEF SUMMARY

The present embodiments relate to application of a conductive coating to an adhesion-resistant surface. In one embodiment, a method of adhering a conductive coating to an adhesion-resistant outer surface is performed. The method includes: applying a primer adhesive to an outer surface of an adhesion-resistant structure; and applying the conductive coating over the primer adhesive.

In some embodiments, the method includes pretreating the outer surface of the adhesion-resistant structure before applying the primer adhesive.

In some embodiments, the method includes: after applying the primer adhesive and before applying the conductive coating, subjecting a combination of the adhesion-resistant structure and the primer adhesive to heat within a predetermined temperature range above room temperature for a time period. For these embodiments, applying the conductive coating over the primer adhesive is performed after the time period expires.

In some embodiments, the time period corresponds to a percentage of crosslinking between the outer surface of the adhesion-resistant structure and the primer adhesive.

In some embodiments, the percentage of crosslinking is less than 100%.

In some embodiments, the method further includes: after applying the conductive coating over the primer adhesive, subjecting a combination of the adhesion-resistant structure, the primer adhesive, and the conductive coating to heat within a second predetermined temperature range above room temperature for a second time period.

In some embodiments, the method further includes: subjecting the combination of the adhesion-resistant structure and the primer adhesive to a pressure within a predetermined pressure range during the time period.

In some embodiments, applying the conductive coating over the primer adhesive is performed without subjecting a combination of the adhesion-resistant structure and the base coating to heat beforehand.

In some embodiments, the outer surface comprises at least one of a fluoropolymer material or a polyolefin material.

In some embodiments, the adhesion-resistant structure includes a catheter of an endoscopic medical device.

In some embodiments, the endoscopic medical device includes a bipolar sphincterotome, and the primer adhesive and the conductive coating longitudinally extend alongside at least a portion of a cutting edge of the bipolar sphincterotome.

In some embodiments, the conductive coating includes functional groups comprising at least one of: epoxide functional groups, amine functional groups, ketone functional groups, or alcohol functional groups.

In some embodiments, the conductive coating includes elongate conductive particles and the primer adhesive is not conductive.

In some embodiments, wherein the conductive coating includes a polymer backbone.

In another embodiment, a medical device includes: an elongate tubular member comprising an adhesion-resistant outer surface; a primer adhesive directly adhered to the adhesion-resistant outer surface; and a conductive coating directly adhered to the primer adhesive.

In some embodiments, the primer adhesive comprises at least one of: epoxy resin, cyanacrylate, thiol, silane, triphenylphosphine, diaminodiphenylmethane.

In some embodiments, the outer surface includes at least one of a fluoropolymer material or a polyolefin material.

In some embodiments, the conductive coating comprises elongate conductive particles.

In some embodiments, the medical device includes a bipolar sphincterotome, and the primer adhesive and the conductive coating longitudinally extend over a distal portion of the elongate tubular member that is configured to curl when a cutting wire of the bipolar sphincterotomes is pulled taut.

In some embodiments, the primer adhesive does not include any conductive particles.

Other embodiments are possible, and each of the embodiments can be used alone or together in combination. Accordingly, various embodiments will now be described with reference to the attached drawings.

DETAILED DESCRIPTION

The present disclosure describes various embodiments of a sphincterotome having a bipolar configuration, otherwise referred to as a bipolar sphincterotome. The present disclosure also describes various example methods of adhering conductive ink to hydrophobic, adhesive, and/or adhesion resistant structures. An application where the example methods may be used is in the manufacture of bipolar electrosurgical medical devices, such as bipolar sphincterotomes, where the structure is an elongate tubular member, such as a catheter. The conductive ink that is applied to the elongate tubular member conducts electrical current during operation of an electrosurgical procedure.

Sphincterotomes may include an elongate tubular member, such as a catheter, and a cutting wire used to cut a sphincter muscle when performing a sphincterotomy. The cutting wire may be coupled to and/or in electrical communication with a radio frequency (RF) generator, such as an electrosurgical unit (ESU). When the RF generator is activated, the RF generator may supply electrical current to the cutting wire, which may cut the sphincter muscle. The electrical current may travel along the cutting wire, through the sphincter muscle, and then along a return path, which completes the circuit.

The return path for sphincterotomes having a monopolar configuration may include a neutral electrode, which may be a solid, neutral electrode, or a split neutral electrode, and which may be positioned on the thigh of the patient undergoing the sphincterotomy. The return path for bipolar sphincterotomes may differ from monopolar sphincterotomes in that, like the cutting wire (i.e., the active path), the return path may be attached to, integrated with, disposed within, or included as part of the catheter.

Figure 1:
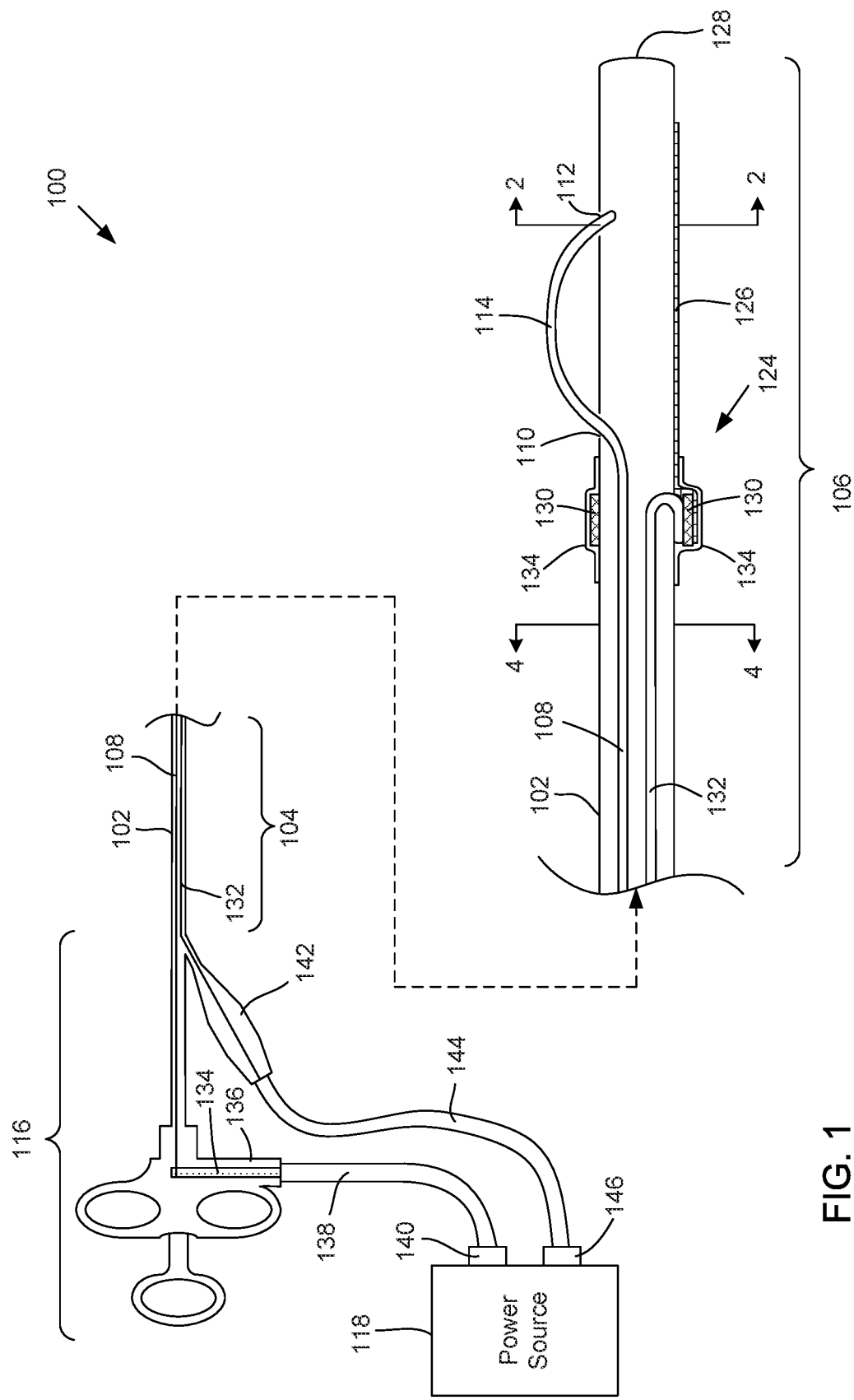
FIG. 1 shows a cross-sectional side view of a bipolar sphincterotome.

FIG. 1 shows a partially cross-sectional side view of an example bipolar sphincterotome 100. The example bipolar sphincterotome 100 may include an elongate, tubular member 102 that has a proximal portion 104 extending to a distal portion 106. A cutting wire 108 used to cut the sphincter muscle may be disposed within a lumen (not shown in FIG. 1) of the tubular member 102 from the proximal portion 104 to the distal portion 106. At the distal portion 106, the cutting wire 108 may extend or protrude from within the tubular member 102, through a first opening 110 of the tubular member 102, to outside the tubular member 102. Outside the tubular member 102, the cutting wire 108 may longitudinally extend substantially parallel with the tubular member 102 to a second opening or anchor point 112 of the tubular member 102 that is distal the first opening 110, where a distal end of the cutting wire 108 may re-enter and/or be fixedly attached to the tubular member 102. The exposed portion 114 of the cutting wire 108 may be referred to as a cutting edge, which may be the portion of the cutting wire 108 that cuts the sphincter muscle.

The bipolar sphincterotome 100 may further include a return path 124. For the bipolar configuration, the return path 124 may be attached to, adhered to, integrated with, disposed within, or included as part of the tubular member 102. In the example embodiment of the bipolar sphincterotome 100, the return path 124 may include conductive material portion 126 disposed on or cover an outer surface of the distal portion 106 of the tubular member 102, and a return wire 132 electrically coupled to the conductive ink portion 126.

In one example embodiment of the return path 124, the conductive material portion 126 may be made of conductive ink (or alternatively referred to as conductive paint or conductive coating). The conductive material portion 126 is hereafter referred to as a conductive ink portion 126, although conductive materials other than ink may be used.

The conductive ink portion 126 may be attached to an outer surface of the tubular member 102 at the distal portion 106. As described in further detail below, the conductive ink portion 126 may be attached to the outer surface of the tubular member 102 by being directly attached to the outer surface, or indirectly attached via a primer adhesive.

The conductive ink portion 126 may extend distally past the anchor point 112. Extending the conductive ink portion 126 distally past the anchor point 112 may ensure or increase the likelihood that the return path 124 contacts the sphincter muscle (or tissue near the sphincter muscle) to make a proper connection at the treatment site. Additionally, the conductive ink portion 126 may distally extend to a position before a distal tip 128 or sufficiently away from an opening of a wire guide lumen (not shown in FIG. 1) at the distal tip 128 so that a wire guide in the wire guide lumen is not part of or is isolated from the return path 124. In addition, the conductive ink portion 126 may proximally extend past the first opening 110.

Figure 4:
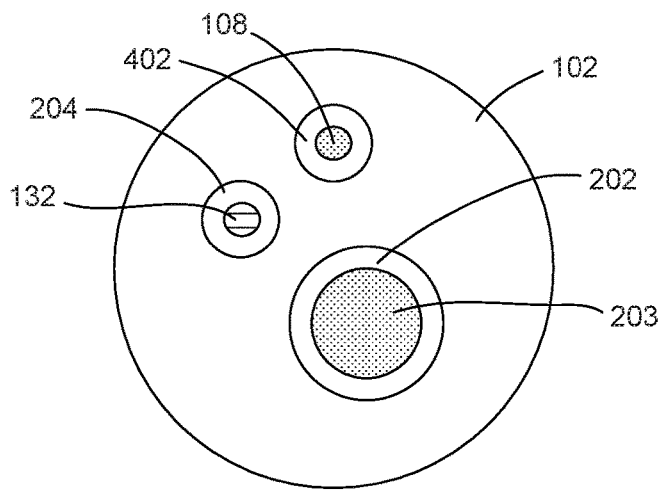
FIG. 4 shows a cross-sectional axial view of the bipolar sphincterotome of FIG. 1 taken proximal a coupling area of a return path, showing a return wire disposed in a lumen having multiple functions.
Figure 5:
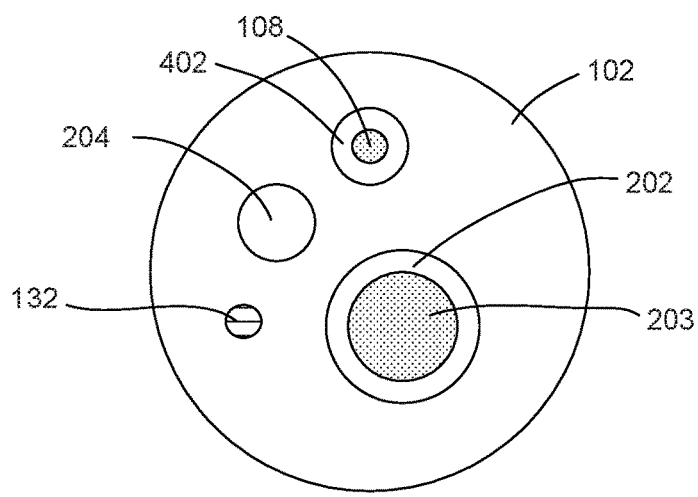
FIG. 5 shows a cross-sectional axial view of an alternative embodiment of the cross-section of the bipolar sphincterotome shown in FIG. 4, where the return wire is embedded in a tubular member of the bipolar sphincterotome.
Figure 6:
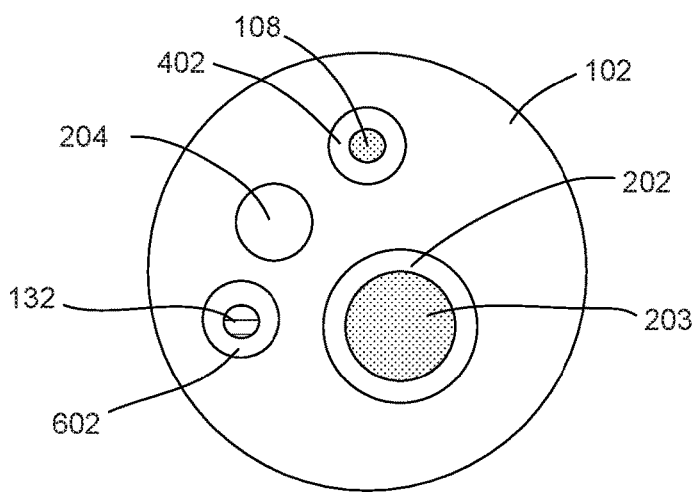
FIG. 6 shows a cross-sectional axial view of another alternative embodiment of the cross-section of the bipolar sphincterotome shown in FIG. 4, where the return wire is disposed in a lumen having a sole function to house the return wire.

The conductive ink portion 126 may be electrically coupled to a return wire 132, which may form and/or be part of the return path 124. The return wire 132 may extend within the tubular member 102 from where the return wire 132 is electrically coupled to the conductive ink portion 126 to the proximal portion 104. The return wire 132 may extend within the tubular member 102 generally or substantially parallel to the cutting wire 108. In addition, the return wire 132 may extend within the tubular member 102 in various locations relative to the cutting wire 108. FIG. 1 shows the active wire 108 and the return wire 132 generally in the same cross-sectional plane. However, as shown in FIGS. 4-6, the return wire 132 may be disposed within the tubular member 102 in various locations relative to the cutting wire 108. Also, as described in more detail below, the return wire 132 may be disposed and/or extend within a lumen of the tubular member 102, or alternatively, may be embedded within and/or coextruded with the tubular member 102.

The conductive ink portion 126 may be electrically coupled to the return wire 132 in various ways. For example, as shown in FIG. 1, the conductive ink portion 126 may proximally extend to a conductive ring or cannula 130, which may electrically couple the conductive ink portion 126 to the return wire 132. In some example embodiments, the conductive cannula 130 may be attached or crimped to the outer surface of the tubular member 102. The conductive cannula 130 may be made of metal, such as stainless steel, silver, gold, tantalum, or tungsten, as examples. The conductive ink may be applied to and/or deposited over and/or under at least a portion of the conductive cannula 130 so that the conductive ink portion 126 and the conductive cannula 130 are electrically coupled, and the conductive cannula 130 is part of the return path 124. As shown in FIG. 1, the return wire 132 may be connected to the conductive cannula 130 to be electrically coupled with the conductive ink portion 126. For example, the return wire 132 may be curled at its distal end to extend to the outer surface of the tubular member 102, and the conductive cannula may be crimped to the tubular member 102 over the distal end of the return wire 132.

In some embodiments, the bipolar sphincterotome 100 may further include a tube 134 disposed over the conductive cannula 130 and the conductive ink that is covering or disposed on the conductive cannula 130. As shown in FIG. 1, the tube 134 may distally extend to the first opening 110 in the tubular member 102, or alternatively to a position in between the cannula 130 and the first opening 110. In some embodiments, the tube 134 may be a shrink tube 134 that conforms to the surface that the shrink tube 134 is covering, such as when heat is applied to the shrink tube 134. The tube 134 may have a thickness of about 0.0002 inches, although other thicknesses may be used. The tube 134 may be disposed over the cannula 130 to provide a relief to the strain caused by varying flexibilities between the tubular member 102 (which may be relatively flexible) and the metal cannula 130 (which may be relatively rigid). Additionally, the tube 134 may provide a protective coating or scratch resistance, which may prevent or minimize the conductive ink from being scratched off.

For some example embodiments of the tube 134, an inner surface of the tube 134 may be coated with one or more conductive materials, such as a conductive ink, a conductive powder, a conductive adhesive, or combinations thereof, as examples. The conductive material may be the same material as or may be a different material then the conductive ink that makes up the conductive ink portion 126. The tube 134, with an inner surface coated with a conductive material, may enhance electrical continuity between the conductive ink portion 126 and the conductive cannula 130.

FIG. 1 shows a part of the conductive ink portion 126 disposed or deposited over the conductive cannula 130 so that the conductive ink portion 126 and the conductive cannula 130 may be electrically connected with each other. In an alternative embodiment of the distal portion 106, the conductive ink portion 126 may be deposited on the outer surface of the tubular member 102 and/or the conductive cannula 130 may be positioned relative to the conductive ink portion so that they are physically separated, and/or so that by themselves, they are electrically disconnected from each other. For this alternative embodiment, the tube 134 with an inner surface being coated with a conductive material may be disposed over both the conductive cannula 130 and the conductive ink portion 126 to electrically connect the conductive ink portion 126 with the conductive cannula 130.

In still other alternative embodiments, the tube 134 may be replaced with an adhesive, an epoxy, a notched cannula, a cannula with a wavy or flexible distal tip, or any combination thereof. In still other alternative embodiments, the tube 134 or other covering or coating may not be included.

Figure 1A:
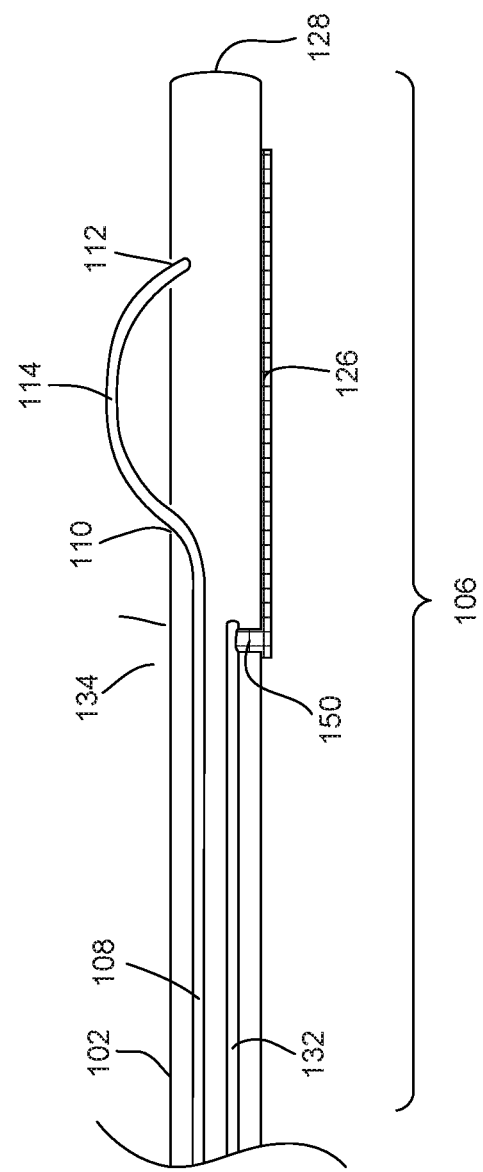
FIG. 1A shows cross-sectional side view of an alternative embodiment of a distal portion of the bipolar sphincterotome shown in FIG. 1.

Referring to FIG. 1A, another alternative example embodiment of the bipolar sphincterotome 100 may include an opening 150 in a wall of the tubular member 102 instead of the metal cannula 130 to electrically couple the return wire 132 with the conductive ink portion 126. The opening 150, such as a skive or a cut in the tubular member 102, may extend from the outer surface of the tubular member 102 to an inner portion where a distal end of the return wire 132 is disposed. The conductive ink portion 126 may be deposited to extend within the opening 150 so that the conductive ink portion 126 is electrically coupled to the return path 132.

Figure 1B:
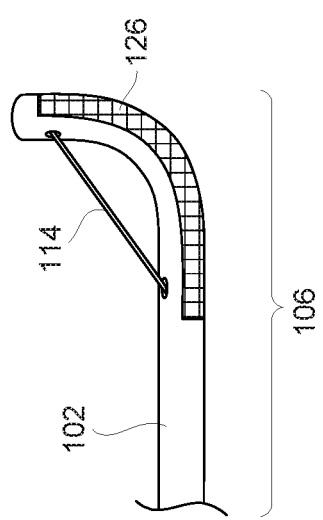
FIG. 1B shows a perspective side view of a distal portion of the bipolar sphincterotomes of FIG. 1 in a curled position, with a cutting edge in a cutting state.

Referring back to FIG. 1, the bipolar sphincterotome 100 may further include a handle assembly 116 coupled to the proximal portion 104 and/or a proximal end of the cutting wire 108. The handle assembly 116 may be operatively coupled to the cutting wire 108 to move the cutting edge 114 between a relaxed state and a cutting state. FIG. 1 shows the cutting edge 114 in the relaxed state and the distal portion 106 in an uncurled position. The handle assembly 116 may be configured to move the cutting edge 114 from the relaxed state to the cutting state by proximally pulling the cutting wire 108 taut. When the cutting wire 108 is pulled, the distal portion 106 of the tubular member 102 may bow or curl, forming an arc. The taut cutting edge 114 may form a secant of the arc. FIG. 1B shows the cutting edge 114 in the cutting state (i.e., taut) and the distal portion 106 of the tubular member 102 in a bowed or curled position. When the distal portion 106 is curled and the cutting edge 114 is taut, the distal portion 106 and the cutting edge 114 may be configured or in position to cut the sphincter muscle. The handle assembly 116 may also be configured to release or distally push the cutting wire 108 to uncurl the distal portion 106 and to move the cutting edge 114 from the taut state to the relaxed state. When the distal portion 106 is uncurled (or at least in a position that is curled to a lesser degree than when the cutting edge 114 is taut) and the cutting edge 114 is in the relaxed state, the distal portion 106 and the cutting edge 114 may not be configured to cut the sphincter muscle and/or may be configured or in position to be moved to and from the treatment site.

Both the cutting wire 108 and the return wire 132 may be electrically coupled to a power source 118, such as a radio frequency (RF) generator or an electrosurgical unit (ESU), that supplies electrical current to the cutting wire 108 to perform the electrosurgery. In one example embodiment, the cutting wire 108 may be electrically coupled to the power source 118 by proximally extending to the handle assembly 116, where the proximal end of the cutting wire 108 may be connected to a metallic pin 134 that extends to a port 136 of the handle assembly 116. The metallic pin 134 and/or the port 136 may be adaptable to connect to supply cabling 138 that may connect to an active port 140 of the power source 118.

The return wire 132 may be electrically coupled to the power source 118 by distally extending through a side port 142 connected to the tubular member 102, where a proximal end of the return wire 132 may be connected to return cabling 144, such as by soldering the return wire with one or more wires of the return cabling 144. Alternatively, the return wire 132 may be connected to the return cabling 144 by crimping the return cabling to the return wire 132 disposed inside a metal cannula. The return cabling 144 may be adaptable to connect to a return port 146 of the power source 118. When the power source 118 is activated, the power source 118 may deliver electric current to the cutting wire 108 via the supply cabling 138 and the metallic pin 134. The electrical current may pass through the cutting wire 108 to the cutting edge 114, where electrosurgery may be performed on sphincter muscle. The electrical current may pass through the sphincter muscle, which acts as a load, and then along the return path 124, including the conductive ink portion 126 and the return path, back to the power source 118 via the return cabling 144.

Figure 2:
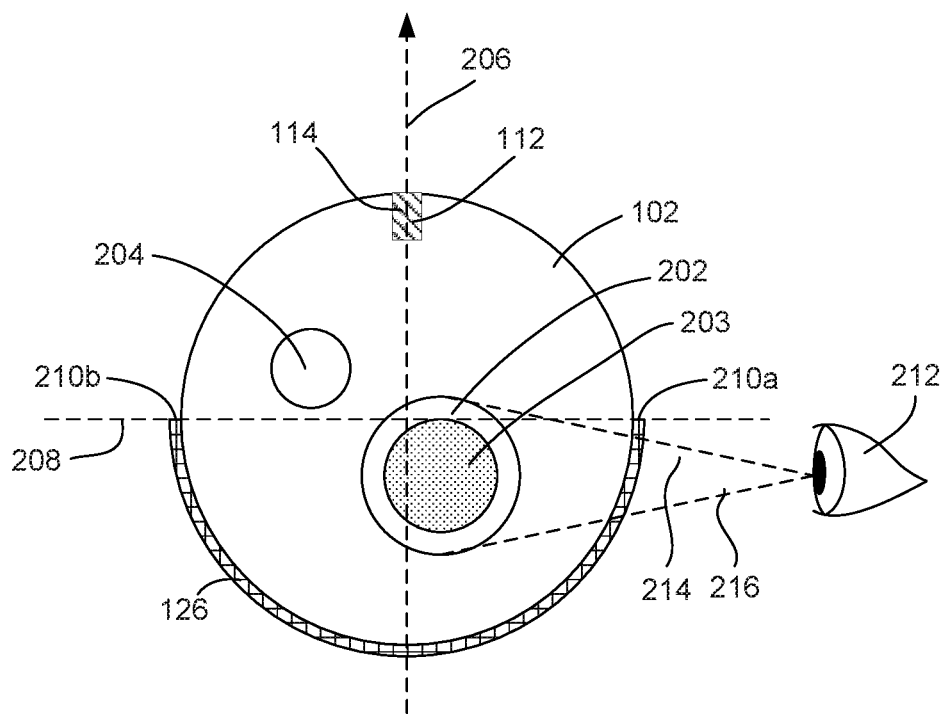
FIG. 2 shows a cross-sectional axial view of the distal portion of the bipolar sphincterotome of FIG. 1, showing a circumferential orientation of a conductive ink portion.

FIG. 2 shows a cross-sectional view of an example embodiment of the bipolar sphincterotome 100 taken along line 2-2 in FIG. 1. The tubular member 102 may include a wire guide lumen 202 that is configured to receive and have movably disposed therethrough a wire guide 203. In operation, the wire guide 203 may be delivered to the treatment site within the patient. The wire guide lumen 202 may be inserted over the wire guide 203, and the distal portion 106 of the bipolar sphincterotome 100 may be delivered to the treatment site. The tubular member 102 may include one or more other lumens, such as an injection lumen 204, which may be used to deliver contrast to the treatment site.

As shown in FIG. 2, the conductive ink portion 126 may be circumferentially disposed partially around the outer surface of the tubular member 102. The circumferential disposition of the conductive ink portion 126 may have an orientation that is defined or determined relative to a radial orientation of the anchor point 112 or the cutting edge 114 of the cutting wire 108. The radial orientation of the anchor point 112 or the cutting edge 114 may be defined by a direction in which the cutting edge 114 radially extends from the tubular member and/or may be identified by a dotted arrow 206, which extends from a center point or origin of the tubular member 102 through the anchor point 112. The orientation of the circumferential disposition of the conductive ink portion 126 may be identified by a dotted line 208 extending through the circumferential ends 210a, 210b of the conductive ink portion 126. The orientation of the circumferential disposition of the conductive ink portion 126 relative to the radial orientation of the anchor point 112 or cutting edge 114 may be defined or determined as a radial difference or difference in degrees between the dotted lines 206 and 208. In one example configuration, as shown FIG. 2, the circumferential disposition of the conductive ink portion 126 may be oriented perpendicular or substantially perpendicular to the radial orientation of the anchor point 112 or the cutting edge 114, as identified by the ninety-degree radial difference or perpendicular intersection between the dotted lines 206 and 208.

The tubular member 102 may be made of a clear, or at least semi-clear, material. The tubular member 102 may be clear or semi-clear for visualization purposes. For example, a side viewing endoscope may provide a physician or other operator of the bipolar sphincterotome 100 visual access to the side of the tubular member 102. The clear material may further provide the physician or operator visual access to inside the tubular member 102, such as visual access to one or more lumens of the tubular member 102. In particular, the clear material may provide visual access to the wire guide lumen 202 so that the physician or operator may see the wire guide 203 move through the wire guide lumen 202.

However, the conductive ink portion 126 may be an opaque or substantially opaque material, which may block or impede visual access to within the tubular member 102, and particularly the wire guide lumen 202. As such, it may be desirable to orient the conductive ink portion 126 around the tubular member 102 in a way that provides for visual access to the wire guide lumen 202. In some example tubular member configurations as shown in FIG. 2, the wire guide lumen 202 may be disposed within the tubular member 102 relative to the anchor point 112 or the wire guide 108 such that a perpendicular orientation of the circumferential disposition of the conductive ink portion 126 relative to the radial orientation of the anchor point 112 or the cutting edge 114 may block or prevent visual access to the wire guide lumen 202. FIG. 2 shows how visual access, represented by eyeball 212 and dotted lines 214, 216, may be blocked by the perpendicular orientation.

Figure 3:
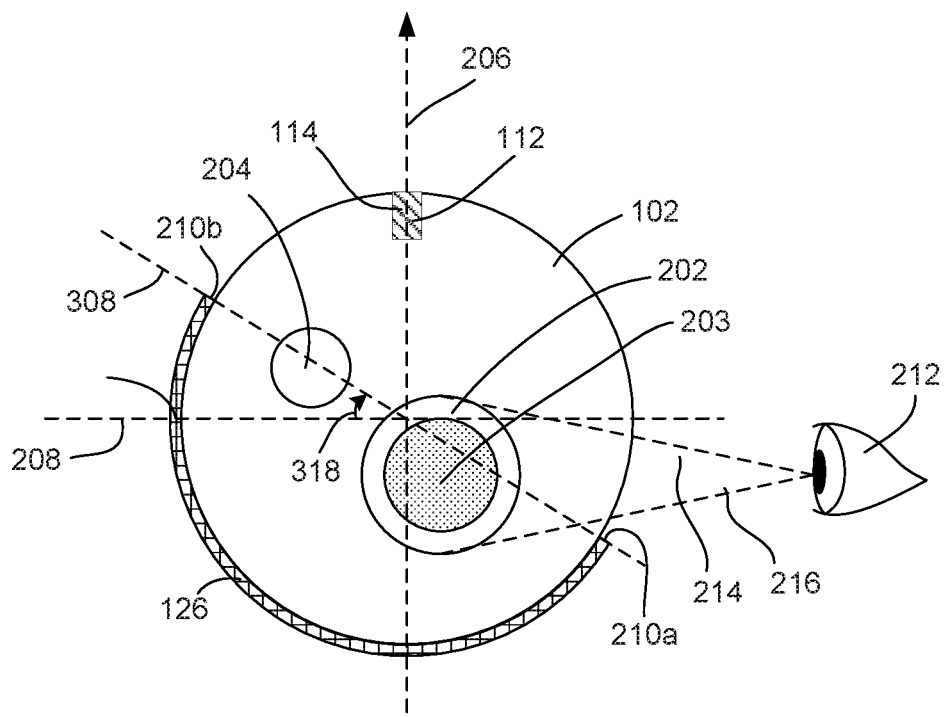
FIG. 3 shows a cross-section axial view of the distal portion of the bipolar sphincterotome of FIG. 1, showing an alternative circumferential orientation of the conductive ink portion.

FIG. 3 shows a cross-sectional view of an alternative embodiment of the bipolar sphincterotome 100 taken along line 2-2 in FIG. 1. In the alternative embodiment shown in FIG. 3, the circumferential disposition of the conductive ink portion 102 may have an orientation that is offset (denoted by dotted line 308) from the perpendicular orientation (denoted by dotted line 208) to unblock or provide visual access to the wire guide lumen 202. In some example configurations, the offset (denoted by arrow 318) may be about thirty-degrees, although any degree offset may be utilized that provides visual access to the wire guide lumen. Also, the direction in which the offset is made may depend on the side of the bipolar sphincterotome 100 to which the side viewing endoscope is configured to have visual access. For example, when looking at the cross-section of the bipolar sphincterotome 100 from the perspective shown in FIG. 3, visual access (denoted by the eyeball 212 and the dotted lines 214, 216), may be on the "right" side. As such, the offset may be in a clockwise direction. Alternatively, if visual access were on the opposite side (e.g., the "left" side from the perspective in FIG. 3), then the offset may be in a counter-clockwise direction.

FIGS. 2 and 3 show that the circumferential disposition of the conductive ink portion 126 extends about halfway around the tubular member (i.e., the dotted line 206 extends through the center or origin of the tubular member 102). In alternative configurations, the circumferential disposition of the conductive ink portion 126 may extend less than halfway or more than halfway around the tubular member.

FIG. 4 shows a cross-sectional view of an embodiment of the sphincterotome 100 taken along line 4-4 in FIG. 1. The cross-sectional view shown in FIG. 4 may be representative of the cross-section of the tubular member 102 proximal the conductive cannula 130. FIG. 4 shows the wire guide 203 disposed within the wire guide lumen, as well as the cutting wire 108 disposed within a cutting wire lumen 402. In addition, as shown in FIG. 4, the return wire 132 may be disposed and extend within the injection lumen 204. As such, the injection lumen 204 may serve a dual role or have two functions—to deliver contrast to the treatment site, and to house the return path 132 of the bipolar sphincterotome 100. Although the embodiment in FIG. 4 shows the return wire 132 disposed within the injection lumen 204, the return wire 132 may be disposed in a different lumen than the injection lumen 204. Generally, the sphincterotome 100 may be configured so that one of a plurality of lumens within the tubular member 102 has dual or multiple purposes or functions, one of which is to house the return wire 132.

FIG. 5 shows a cross-sectional view of an alternative embodiment of the bipolar sphincterotome 100 taken along line 4-4 in FIG. 1. In the alternative embodiment, the return wire 132 may be embedded within and/or an integral part of the tubular member 102, rather than be disposed within the injection lumen 204. As such, none of the lumens in the tubular member 102 may function to house the return wire 132. In this alternative embodiment, the tubular member 102 and the return wire 132 may be co-extruded to embed or integrate the return wire 132 with the tubular member 102.

FIG. 6 shows a cross-sectional view of a second alternative embodiment of the bipolar sphincterotome 100 taken along line 4-4 in FIG. 1. In the second alternative embodiment, the tubular member 102 includes a lumen 602 having a single function or purpose to house the return wire 132.

Figure 7:
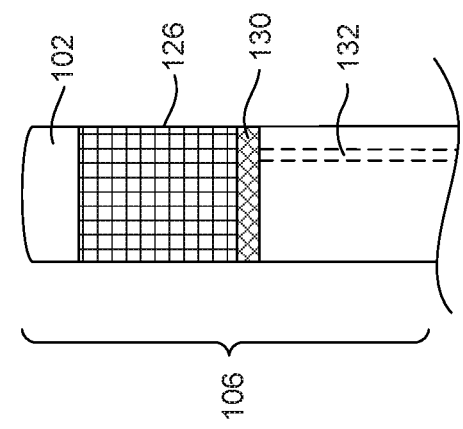
FIG. 7. shows a side view of the distal portion of the bipolar sphincterotome of FIG. 1, where the return path is a single return path.

In some example embodiments, the return path 124 may include a single return path. For these example embodiments, the conductive ink portion 126 may include a single, continuous portion electrically coupled to a single return wire 132. FIG. 7 shows a side view of an example embodiment of the distal portion 104 from an angle showing most if not all of the conductive ink portion 126, where the return path 124 is a single return path.

In alternative example embodiments, the return path 124 may include multiple, such as two, return paths. The multiple return paths may be electrically isolated or substantially electrically isolated from each other. Multiple return paths may be included to provide a safety feature for the bipolar sphincterotome 100. Some power sources 118 (FIG. 1) may be configured for dual return paths in that the power sources 118 may be configured to prevent output of the electrical current unless each of the return paths are in contact with the sphincter muscle or the surrounding tissue. This ensures adequate placement of the distal portion at the treatment site before the electrical current may be supplied from the power source 118. Additionally, if any of the return paths becomes disconnected, such as through fracture or burnout, the power source 118 may be configured to detect or recognize the disconnection and prevent the electrical current from being supplied to the treatment site.

Figure 8:
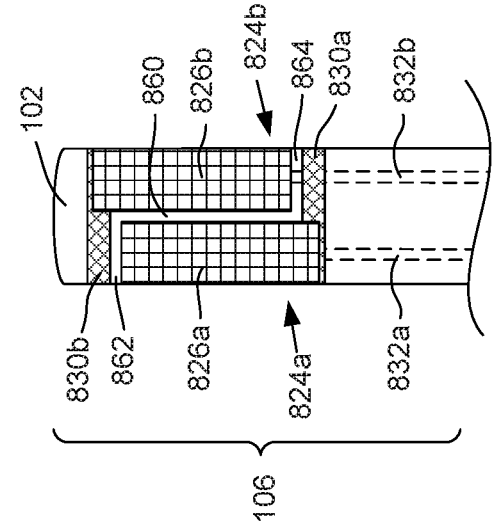
FIG. 8. shows a side view of an alternative embodiment of the distal portion of the sphincterotome of FIG. 1, where the return path includes two return paths and where a gap separating two conductive ink portions extends in a substantially straight direction.

FIG. 8 shows a side view of an example embodiment of the distal portion 106 from an angle showing most if not all of the conductive ink portion 126, where the return path includes a dual return path. The dual return path may include a first return path 824a and a second return path 824b. To form the first and second paths 824a, 824b, the conductive ink portion 126 may include two sub-portions or strips, including a first sub-portion 826a and a second sub-portion 826b. The first sub-portion 826a and the second sub-portion 826b may be electrically isolated from each other. The conductive ink making up the first and second sub-portions 826a, 826b may be deposited to form a gap or spacing 860 in between the first and second sub-portions 826a, 826b to electrically isolate the first and second sub-portions 826a, 826b from each other. In some example configurations, a width of the gap 860 may be about 0.040 inches, although other sizes for the width may be used.

The first and second sub-portions 826a, 826b may each be electrically coupled to a respective return wire. For example, the first sub-portion 826a may be electrically coupled to a first return wire 832a and the second sub-portion 826b may be electrically coupled to a second return wire 832b. In some example embodiments, the first and second sub-portions 826a, 826b may be electrically coupled to their respective return wires 832a, 832b at opposing ends of the sub-portions 826a, 826b. Additionally, the first and second sub-portions 826a, 826b may be electrically coupled to their respective return wires 832a, 832b in various ways, such as those described above. For example, as shown in FIG. 8, two metal cannulas 830a, 830b may be used to electrically couple the sub-portions 826a, 826b with their respective return wires 832a, 832b. The metal cannulas 830a, 830b may be disposed at opposing ends of the conductive ink portion 126 such that only one of the sub-portions 826a, 826b is coupled to each of the metal cannulas 830a, 830b. To do so, the second sub-portion 826b may distally extend past the first sub-portion 826a so that the second sub-portion 826b is electrically connected to the metal cannula 830b, and a gap 862 electrically isolates the second sub-portion 826b from the metal cannula 830a. Similarly, the first sub-portion 826a may proximally extend past the second sub-portion 826b so that the first sub-portion 826a is electrically connected to the metal cannula 830a, and a gap 864 electrically isolates the first sub-portion 826a from the metal cannula 830b. In other example embodiments, one or both of the metal cannulas 830a, 830b may be replaced with an opening in the tubular member 102 (such as the opening 150 shown in FIG. 1A). The conductive ink making up the first sub-portion 826a may extend into one of the openings to be electrically coupled with the first return wire 832a. Similarly, the conductive ink making up the second sub-portion 826b may extend into the other opening to be electrically coupled with the second return wire 832b.

The return wires 832a, 832b may be disposed within the tubular member in various combinations of the embodiments shown in cross-section in FIGS. 4-6. For example, one of the return wires 832a, 834b may be disposed within one of the lumens, such as the injection lumen, so that one of the lumens serves a dual purpose as described above. The other of the return wires 832a, 832b may be embedded as an integral component of the tubular member 102. Alternatively, one of the return wires 832a may be disposed within a lumen serving a dual purpose and the other return wire 832b may be disposed within a lumen having a sole purpose to house the return wire 832b. Alternatively, both of the return wires 832a, 832b may be embedded within the tubular member 102, or each of the return wires 832a, 832b may be disposed in respective lumens, each of which has a sole purpose of housing the return wire 832a or 832b. Various configurations are possible. In the tubular member 102, the return wires 832a, 832 may longitudinally extend parallel or substantially parallel to each other.

Figure 10:
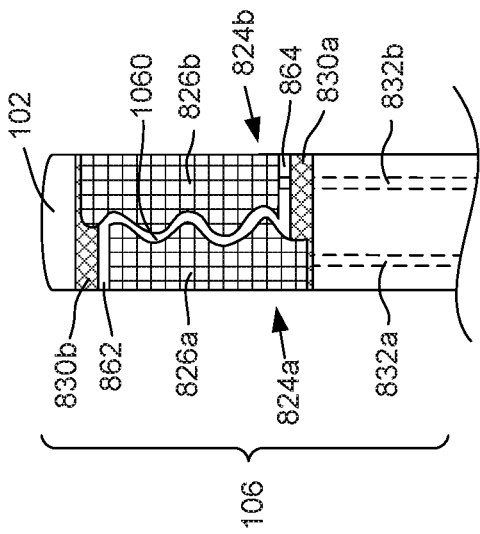
FIG. 10. shows a side view of a third alternative embodiment of the distal portion of the sphincterotome of FIG. 1, where the return path includes two return paths and where the gap has a sinusoidal pattern.
Figure 9:
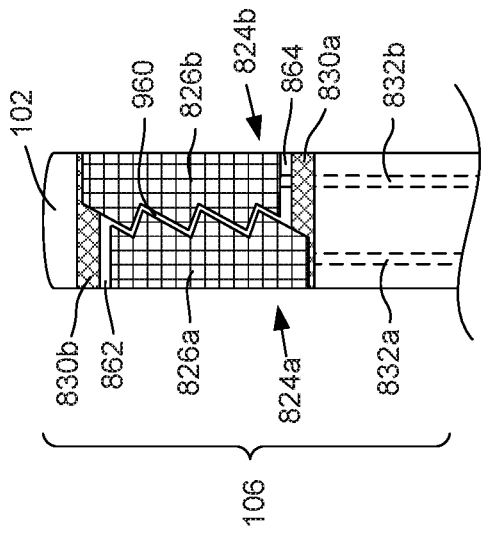
FIG. 9. shows a side view of a second alternative embodiment of the distal portion of the sphincterotome of FIG. 1, where the return path includes two return paths and where the gap has a zig-zag pattern.

In one example configuration, as shown in FIG. 8, the gap 860 separating and electrically isolating the first and second sub-portions 826a, 826b may longitudinally extend along the outer surface of the distal portion in a straight or substantially straight direction. In alternative configurations, the gap may longitudinally extend in a non-straight manner. For example, as shown in FIG. 9, a gap 960 may have a zig-zag pattern. As another example, referring to FIG. 10, the gap 1060 may have a sinusoidal pattern. Various other patterns may be used for the gap, such as helical or spiral, as examples. Alternatively, the gap may not necessarily have a pattern, but may extend in a generally non-straight manner along the outer surface of the distal portion 106. Configuring the gap to extend in a non-straight manner or have a non-straight pattern may be advantageous over configurations where the gap extends straightly in that the non-straight configurations may facilitate contact for both the first and second sub-portions of the conductive ink with the sphincter muscle or surrounding tissue.

Referring back to FIG. 1, the return cabling 144 may be configured to connect to various types or configurations of the power source 118 and/or of the return port 146 of the power source 118. In many situations, the power source 118 used to connect to the bipolar sphincterotome 100, may have been configured, such as when manufactured, to connect to and/or receive return cabling for monopolar sphincterotomes, which may use a solid neutral electrode or a split neutral electrode as part of the return path. Some power sources 118 may be configured to receive and/or connect to a single return path (e.g., a monopolar sphincterotome that uses a solid neutral electrode), two return paths (e.g., a monopolar sphincterotome that uses a split neutral electrode), or both.

For the bipolar sphincterotome configurations, the return cabling 144 electrically coupling the return path 124 to the return port 146 of the power source 118 may be configured in various ways to accommodate both the single and dual path configurations of the bipolar sphincterotome 100 as well as a power source 118 configured to recognize a solid neutral electrode, a split neutral electrode, or both.

Figure 11:
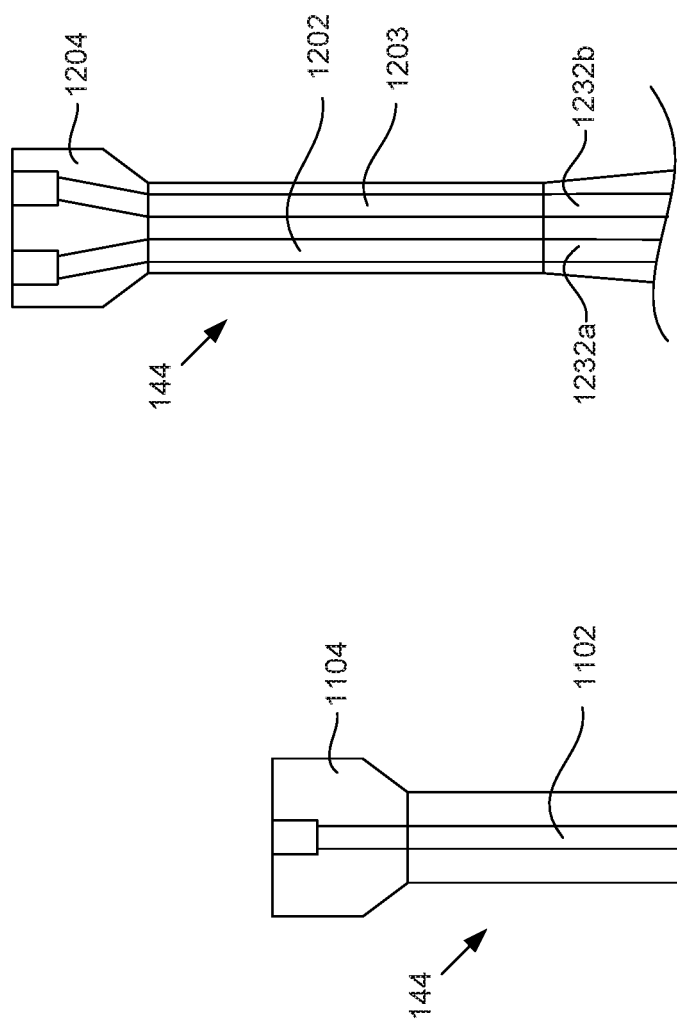
FIG. 11. shows a cross-sectional view of cabling electrically coupling a single return wire with a single wire in the cabling.

Referring to FIG. 11, where the bipolar sphincterotome 100 includes a single return path, to connect to a power source 118 that is configured to recognize a solid neutral electrode, the return cabling 144 may include a single wire 1102 that is connected to a single return wire 132. The wire 1102 may proximally terminate at a plug 1104 that is adaptable to connect and electrically couple the wire 1102 to the return port 146 of the power source 118.

Figure 12:
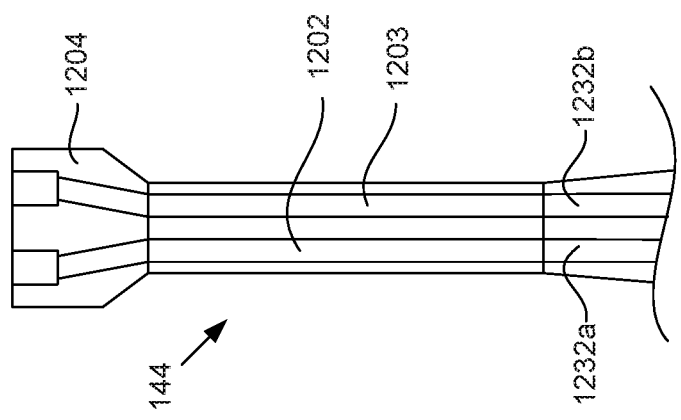
FIG. 12. shows a cross-sectional view of an alternative embodiment of the cabling of FIG. 11, where the cabling includes two wires, each electrically coupled to a return wire.

Referring to FIG. 12, where the bipolar sphincterotome 100 includes two return paths, to connect to a power source 118 that is configured to recognize a split neutral electrode, the return cabling 144 may include two wires 1202, 1203 electrically isolated from each other. One of the wires 1202 in the return cabling 144 may be connected to one of the return wires 1232a, and the other wire 1203 in the return cabling 144 may be connected to the other return wire 1232b. Each of wires 1002, 1003 may proximally terminate at a plug 1204 that is adaptable to connect and electrically couple the wires 1202, 1203 to the return port 146.

Figure 13:
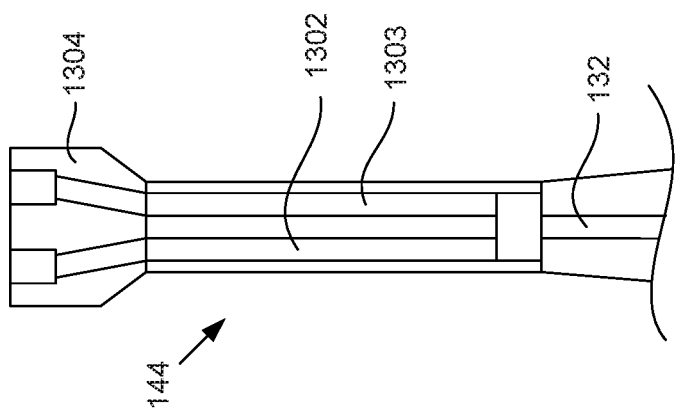
FIG. 13 shows a cross-sectional view of a second alternative embodiment of the cabling of FIG. 11, where the cabling includes two wires shorted together and electrically coupled to a single return wire.
Figure 14:
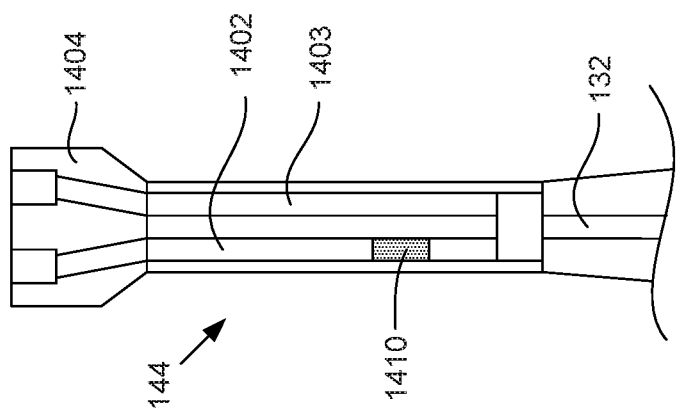
FIG. 14 shows a cross-sectional view of a third alternative embodiment of the cabling of FIG. 11, where the cabling includes two wires, and where one of the wires includes a resistive element.

For some power sources 118, the return port 146 may be configured to connect to two return paths, even though the power source 118 may be configured to recognize a solid neutral electrode. For these configurations, the return cabling 144 may include two wires that are configured so that the power source 118 recognizes a solid neutral electrode. Referring to FIG. 13, where the bipolar sphincterotome 100 includes a single return path, to connect to a power source 118 that is physically configured to receive two return paths but is also configured to recognize a solid neutral electrode, the return cabling 144 may include two wires 1302, 1303 that are shorted together at a distal end of the wires 1302, 1303, where they also may be connected to a proximal end of the single return wire 132. Each of wires 1302, 1303 may proximally terminate at a plug 1304 that is adaptable to connect and electrically couple the wires 1302, 1303 to the return port 146. For this configuration, the power source 118 may determine or recognize a nominal resistance between the two return paths, just as it would for a solid neutral electrode.

Where the return port 146 is configured to connect to two return paths, and the power source 118 is configured to recognize a split neutral electrode, a resistance may be included in one of the wires in the return cabling 144 where the return path 124 of the bipolar sphincterotome includes a single return path. Referring to FIG. 14, a resistive element or resistor 1410 may be added to or included in one of wires 1402, 1403 of the return cabling 144 so that a resistance exists between the two wires 1402, 1403. The wires 1402, 1403 may then be connected together at their distal ends, where they may be connected to the single return wire 132. The resistance chosen for the resistive element 1410 may be in range that the power source 118 may be configured to measure or recognize the bipolar sphincterotome 100 as using a split neutral electrode. In some examples, the range may be about 5-150 Ohms, although other resistances may be used depending on the power source 118. The value of the resistance may be optimized to work for multiple or various types of power sources 118.

Alternatively, the resistance for the resistive element 1410 may be a value that may cause the power source 118 to recognize the bipolar sphincterotome 100 as using either a solid neutral electrode or a split neutral electrode. Some power sources 118 are configured to use an upper limit for resistance that the power source 118 may accept to recognize a solid neutral electrode, while also having a lower limit for resistance that the power source 118 may accept to recognize a split neutral electrode. For these power sources 118, if there is an overlap between the upper and lower limits, the resistance for the resistive element 1410 may be chosen in the overlap, and no errors may be identified by the power source 118 whether the power source 118 is set to recognize either a solid neutral electrode or a split neutral electrode.

Figure 15:
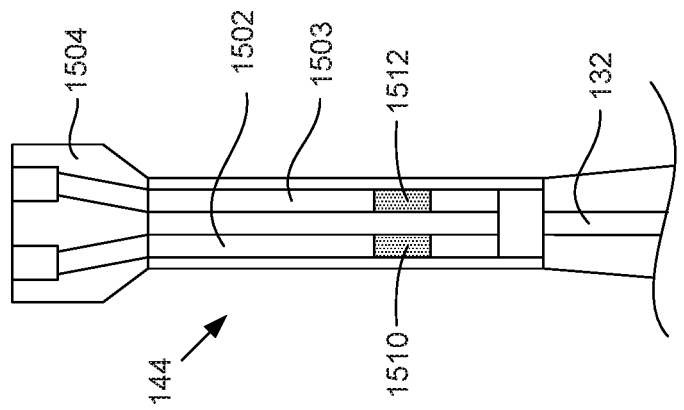
FIG. 15 shows a cross-sectional view of a fourth alternative embodiment of the cabling of FIG. 11, where the cabling includes two wires, and where each of the wires includes a resistive element.

In an alternative embodiment, resistive elements may be included in both of the wires in the cabling. Referring to FIG. 15, a resistive element 1510 may be included in a wire 1502, and a resistive element 1512 may be included in a wire 1503 of the return cabling 144. The sum of the resistances of the resistive elements 1510, 1512 may be equal to a resistance of a single resistive element where only one of the wires includes a resistive element (e.g., resistive element 1410 shown in FIG. 14). Additionally, the resistances of the resistive elements 1510, 1512 may be the same or substantially the same. Resistive elements 1510, 1520 may be included in both of the wires 1502, 1503 in order to split the power between the two wires 1502, 1503. Heat generated by the two resistive elements 1510, 1512 may be reduced, compared to the single resistive element configuration shown in FIG. 14, because less power may be drawn through each of the resistive elements 1510, 1512. Using two resistive elements 1510, 1512 may also minimize or eliminate polarity in the return path, which may pose safety or performance problems for the sphincterotome.

Referring back to any of FIGS. 1-3, 7-10, the backbone of the conductive ink portion 126 may be a polymer, such as polyester, vinyl, or a combination thereof. Additionally, the conductive ink portion 126 may have a thickness in a range of about 20-40 micrometers (microns), although other thicknesses may be used, including up to 500 microns. In addition or alternatively, the conductive ink, in liquid form, may have a viscosity of about 250 centipoise (cP), although other viscosities may be used, including up to about 10,000 cP.

The conductive ink portion 126 may include conductive particles suspended in the polymer. The conductive particles of the conductive ink may have a size in a range of about 3-30 microns. In addition or alternatively, the conductive particles may be made of a conductive material, such as but not limited to silver, platinum, gold, copper, aluminum, tungsten, or a combination thereof. In addition or alternatively, the conductive particles may have a percent weight of a weight of the conductive ink portion 126 in a range of about 20-90%. The percent weight may or may not be uniform throughout the conductive ink portion 126. In addition or alternatively, the conductive particles in the polymer ink may provide the conductive ink portion 126 with a resistance in a range of about zero (or substantially zero) to ten Ohms, when measured longitudinally.

Figure 16A:
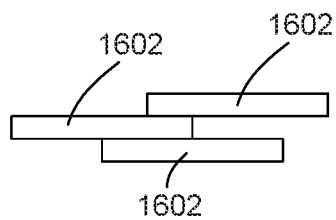
FIG. 16A shows a side view of elongate conductive particles connected to each other in a polymer and when a distal portion of the bipolar sphincterotome of FIG. 1 is in a straightened configuration.
Figure 16B:
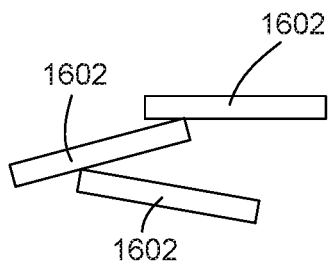
FIG. 16B shows a side of the elongate conductive particles connected to each other in the polymer when the distal portion is in a curled configuration.

Referring to FIGS. 16A and 16B, for some example embodiments, the conductive particles may be elongate structures in that they extend longer in one direction compared to at least one of the other directions. Example elongate structures may include flake-shaped or otherwise thin or planar structures, rods or rod-shaped structures (e.g., nanorods), or wires or wire-shaped structures (e.g., nanowires), or a combination thereof, as non-limiting examples. Elongate structures used for the conductive particles may be contrasted from spherical structures. As previously described, the distal portion 106 of the sphincterotome 100 may be configured to bend or bow from a generally straight or uncurled position (see FIG. 1) into a bowed or curled position (see FIG. 1B). When the distal portion 106 of the tubular member 102 curls, the conductive ink portion 126 curls in conformance with the distal portion 106, as shown in FIG. 1B. By being elongate as opposed to spherical, the conductive particles may have a higher likelihood of remaining in contact with each other when the distal portion 106 curls compared to if they are spherical structures. FIG. 16A shows an example orientation of three elongate conductive particles 1602 connected to each other when suspended in the polymer and when the distal portion 106 is in an uncurled or generally straightened configuration (e.g., when the cutting edge 114 is in the relaxed state as shown in FIG. 1). FIG. 16B shows an example orientation of the three elongate particles 1602 remaining in contact with each other when the distal portion 106 is in a curled configuration (e.g., when the cutting edge 114 is pulled taut and in the cutting state, as shown in FIG. 1B). The curling and uncurling movement of the distal portion 106 may cause the conductive particles 1602 to change their orientation relative to each other. However, despite the change, the conductive particles 1602 may remain in contact with each other due to their elongate shape. In contrast, if the conductive particles 1602 were to have spherical or other non-elongate shapes, they may not stay in contact with each other when the distal portion 106 moves into the curled configuration.

An example conductive ink, which may or may not include all of the above-described properties, may be AG-510 Silver Filled Electrically Conductive Screen Printable Ink/Coating by Conductive Compounds, Inc.

The tubular member 102 may be made of various materials or combinations of materials. The material or combination of materials of the tubular member 102 may be hydrophobic (or have a high degree of hydrophobicity), be adhesion-resistant, and/or have a non-stick outer surface. Hydrophobic materials, as opposed to hydrophilic materials, are repelled by and/or have an inability to be wet by water or water-containing substances. Also, for some example embodiments, adhesion-resistant surfaces can be defined as surfaces with a surface free energy of less than or equal to about 36 milliNewtons per meter (mN/m). Example materials that exhibit hydrophobic, adhesion-resistant, and/or non-stick properties include fluoropolymer (such as polytetrafluoroethylene (PTFE), perfluoroalkoxy (PFA), or fluorinated ethylene propylene (FEP)), or polyolefin (such as polyethylene), as examples. While such materials may be suitable and/or advantageous for endoscopic medical procedures, due to their hydrophobic and/or adhesive properties, such materials do not naturally adhere to, or at least exhibit a sufficient amount of adhesion toward, ink or other similar coatings, such as a conductive polymer-based ink making up the conductive ink portion 126.

Despite the natural repellant properties of hydrophobic and/or adhesion-resistant materials to adhere to conductive ink, the conductive ink portion 126 may be attached to the outer surface of the tubular member 102 using one or a combination of the following: including functional groups in the conductive ink, pretreating the outer surface of the tubular member 102, applying a primer adhesive or base ink to the outer surface of the tubular member 102 before applying the conductive ink, or mechanically bonding the conductive ink and/or the primer adhesive to the outer surface of the tubular member 102. Using one or more of these techniques may allow the conductive ink to sufficiently adhere and/or be attached to the outer surface of the tubular member 102 despite the tubular member 102 being made of a hydrophobic, adhesion-resistant, and/or non-stick material.

Accordingly, using one or a combination of these techniques, the conductive ink portion 126 may be adhered to the outer surface of the tubular member 102 by either being in direct contact and/or directly bonded to the outer surface of the tubular member 102, or by being in indirect contact and/or indirectly bonded to the outer surface of the tubular member 102 via a primer adhesive. Embodiments where the conductive ink portion 126 is in direct contact or directly bonded to the outer surface of the tubular member 102 may be referred to as single-layer embodiments, and embodiments where the conductive ink portion 126 is in indirect contact or indirectly bonded to the outer surface of the tubular member 102 via a primer adhesive may be referred to as a double-layer or multi-layer embodiment.

Figure 17:
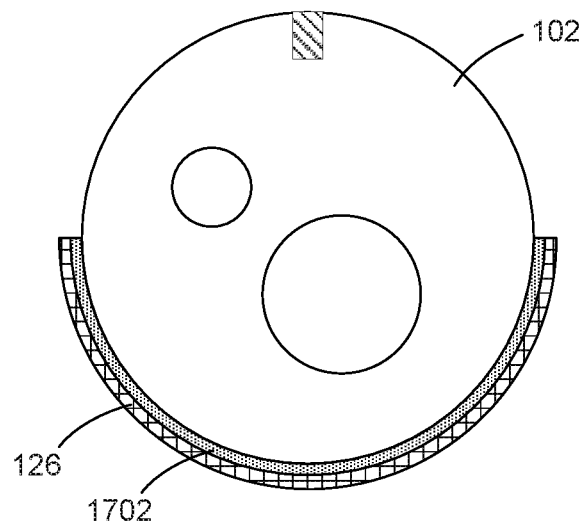
FIG. 17 shows a cross-sectional axial view of the distal portion of the bipolar sphincterotome of FIG. 1, showing a primer adhesive disposed in between an outer surface of the elongate tubular member and the conductive ink portion.

FIGS. 2 and 3 show an example single-layer embodiment where the conductive ink portion 126 is in direct contact and/or directly bonded to the outer surface of the tubular member 102. FIG. 17, shows an example double-layer embodiment where a primer adhesive (or alternatively referred to as a primer or base coating or ink) may be adhered or applied to the tubular member 102 before the conductive ink is applied. As shown in FIG. 17, the primer adhesive may be and/or may form a primer or base layer 1702 that is directly adhered to the adhesion-resistant outer surface of the tubular member 102. The primer adhesive 1702 may be made of a material that has characteristics or qualities that enable it to be adhesive and/or bond to both the material of the tubular member 102 and to the conductive ink 126. Example materials for the primer adhesive may include epoxy resin, cyanoacrylate, thiol, silane, triphenylphosphine, diaminodiphenylmethane, or a combination thereof. Other or additional materials that may bond to the outer surface of the tubular member 102 may be possible. Also, in some of these example embodiments, an antifoaming surfactant may be included in the primer adhesive to minimize air bubbles. The conductive ink may then be applied over the primer adhesive, as described in further detail below. In this way, the primer adhesive 1702 may be an inner or base layer disposed in between the outer surface of the tubular member 102 and the conductive ink portion 126, having a first interface that is directly bonded or in direct contact with the outer surface of the tubular member 102, and a second, opposing interface that is directly bonded or in direct contact with the conductive ink portion 126.

Double-layer or multi-layer embodiments, such as the one described with reference to FIG. 17, may be of higher quality compared to single-layer embodiments, in terms of adhesion and durability. As mentioned, the single conductive layer may include both functional groups and conductive particles. In general, the more functional groups included in the conductive ink, the greater the adhesive quality of the conductive ink. Likewise, the more conductive particles included in the conductive ink, the greater the conductivity of the conductive ink. As such, there may be a tradeoff between the adhesiveness and the conductivity of the conductive ink. That is, increasing the adhesiveness of the conductive ink by increasing the amount of functional groups may result in a decrease in the amount of conductive particles and in turn a decrease in the conductive ink's conductivity. Conversely, increasing the conductivity of the conductive ink by increasing the amount of conductive particles may result in a decrease in the amount of functional groups and in turn a decrease in the conductive ink's adhesiveness. As such, when only a single layer that combines the functional groups and the conductive particles is used, less than optimal adhesive and/or conductivity characteristics of the conductive ink may result, especially for applications where the underlying structure flexes or bends during use, such as the distal portion 106 of the tubular member 102 of the bipolar sphincterotome 100.

Using two layers instead of a single layer, where the primer adhesive does not have, or at least has a lesser amount of conductive particles, may reduce or minimize the undesirable effects of the tradeoff between adhesiveness and conductivity that may be experienced with a single layer. In particular, the primer adhesive may enhance or increase the adhesiveness or bond between the outer surface of the tubular member 102 and the conductive ink 126, which may prevent or reduce the ability for the conductive ink to be rubbed off or otherwise removed from tubular member 102. At the same time, the percent weight of conductive particles making up the conductive ink may be high enough so that the conductive ink has a sufficiently high amount of conductivity, such as a conductivity yielding a resistance in a range of 0 to 10 Ohms, as previously described. As such, the double-layer embodiments may provide an overall coating over the outer surface that has a more optimal combination of adhesiveness and conductivity, compared to a single-layer coating. As with application of a single layer, in some example methods, the outer surface of the tubular member 102 may be pretreated before the primer adhesive is applied in order to facilitate covalent and/or electrostatic bonding.

As described in further detail below, various types of bonding may occur to attach the primer adhesive 1702 or the conductive ink portion 126 to the outer surface of the tubular member 102, including covalent bonding, electrostatic bonding (or other similar forms of non-covalent bonding), mechanical bonding, or a combination thereof. Covalent bonding may hold atoms together to form molecules. Non-covalent or electrostatic bonding may bond molecules together due to the chemical makeup and/or charge of the molecules. Example types of electrostatic bonding may include hydrogen bonding, bonding through van der Waal interactions, or bonding through dipole interactions, as non-limiting examples. Mechanical bonding may bond molecules together as a result of heat, pressure, or a combination of heat and pressure being applied to the molecules.

Functional groups may be included in the conductive ink and/or the primer adhesive to facilitate covalent or electrostatic bonding. Example functional groups or types of functional groups may include epoxide functional groups, amine functional groups, ketone functional groups, and alcohol functional groups, as non-limiting examples. One or a combination of types of functional groups may be included in the conductive ink and/or the primer adhesive. Additionally, electrostatic bonding may depend on whether the functional groups are polar functional groups (i.e., the functional group molecules have a partial negative charge and a partial positive charge for a net neutral charge) or charged function groups (i.e., the functional group molecules have a full charge that is net positive or net negative).

FIGS. 18-24 show example methods of adhering a conductive ink portion (e.g., the conductive ink portion 126) to an outer surface of an elongate tubular member (e.g., the outer surface of the elongate tubular member 102). The example methods described with reference to FIGS. 18-20 include application of a conductive material directly to the outer surface to form a single conductive layer. The method in FIG. 18 uses covalent and/or electrostatic bonding to bond the conductive ink portion directly to the outer surface of the tubular member. The method in FIG. 19 uses mechanical bonding to bond the conductive ink portion directly to the outer surface of the tubular member. The method in FIG. 20 uses a combination of covalent and/or electrostatic bonding and mechanical bonding to bond the conductive ink portion directly to the outer surface of the tubular member.

In addition, the example methods described with reference to FIGS. 21-24 include application of two materials, including application of a primer adhesive directly to the outer surface of the tubular member 102 to form a base or inner layer (e.g., layer 1702 shown in FIG. 17), and application of a conductive ink to the primer adhesive to form an outer conductive layer (e.g., the outer conductive ink layer 126 in the embodiment of FIG. 17). The methods in FIGS. 21 and 22 each use covalent and/or electrostatic bonding to bond the primer adhesive and the conductive ink to each other and to the outer surface of the tubular member. The methods differ from each other in that the method in FIG. 21 includes a separately designated curing phase for the primer adhesive. The method in FIG. 23 uses mechanical bonding to bond the primer adhesive and the conductive ink to each other and to the outer surface of the tubular member. The method in FIG. 24 uses a combination of covalent and/or electrostatic bonding and mechanical bonding to bond the primer adhesive and the conductive ink to each other and to the outer surface of the tubular member.

Figure 18:
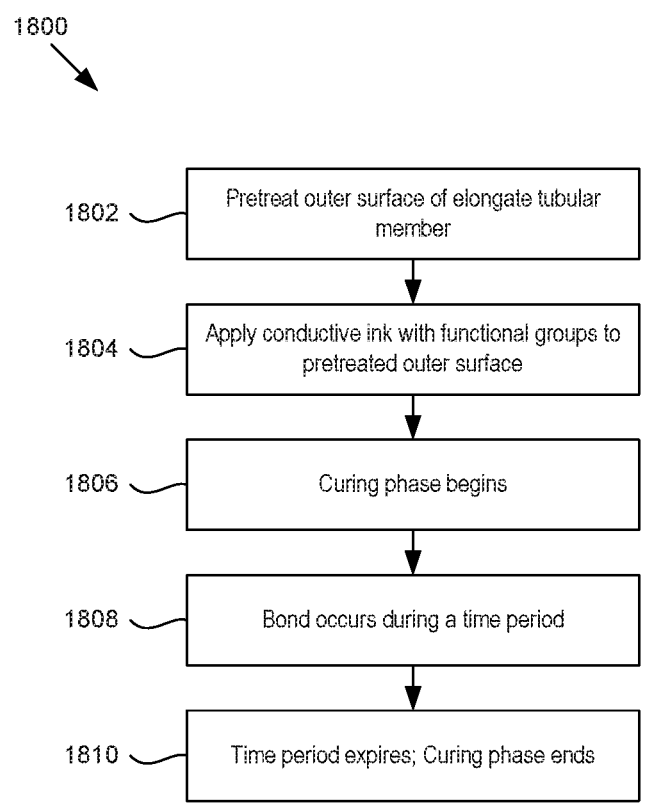
FIG. 18 is a flow chart of an example method of adhering conductive ink directly to an outer surface of a tubular member.

In further detail, FIG. 18 is a flow chart of an example method 1800 in FIG. 18 of adhering a conductive ink portion to an elongate tubular member using covalent and/or electrostatic bonding to bond a single conductive ink layer directly to the outer surface of the tubular member. At block 1802, at least a portion of the outer surface of the tubular member where the conductive ink is to be applied may be pretreated. The pretreatment may be performed to functionalize the outer surface in order to enhance the ability of the outer surface to bond with the conductive ink. For example, the pretreatment may be performed in order for the order surface to enhance the outer surface's ability to chemically react or bond with the conductive ink. One or more of various types of chemical-based pretreatments and/or physical-based pretreatments may be performed on the outer surface before the conductive ink is applied. Chemical-based pretreatments may include wet chemical etching (e.g, with liquid ammonia or tetrahydrofuran based salts or other type of fluoroetchant), pretreatment with aqueous bases, pretreatment with metal amalgams, pretreatment with benzoin dianion reduction, pretreatment with electrochemical reduction, photochemical pretreatment, or plasma pretreatment, as non-limiting examples. Physical-based pretreatments may include sanding, sand blasting, ion sputtering, or vacuum ultraviolet ablation, as non-limiting examples.

After the outer surface of the tubular member is pretreated, then at block 1804, conductive ink comprising functional groups may be applied to the pretreated outer surface. As previously described, a backbone of the conductive ink may be a polymer, such as polyester, vinyl, or a combination thereof, and the ink may be conductive in that conductive particles may be suspended in the polymer. The polymer backbone may also include functional groups, such as epoxide, amine, alcohol, ketone, or a combination thereof. Also, the conductive ink may be applied to the pretreated outer surface in various ways, including pad printing, dipping, rolling, scraping, spraying, or electroplating, as non-limiting examples.

After the conductive ink is applied to the pretreated outer surface at block 1804, a curing phase of the example method 1800 may begin at block 1806. In the curing phase, covalent and/or electrostatic bonds may form between the molecules of the conductive ink and the molecules of the pretreated outer surface in order to directly adhere the conductive ink to the outer surface. Also, solvents originally part of the conductive ink may evaporate during the curing phase.

At block 1808, during the curing phase, a time period may elapse during which the covalent and/or electrostatic bonds may form. In some example methods, during the curing phase, the tubular member and conductive ink combination may be placed inside a chamber, where it is subjected to a vacuum, heat above room temperature, or a combination thereof. Application of the vacuum and/or heat may activate and/or accelerate the bonding during the curing phase. In other example methods, during the curing phase, the tubular member and conductive ink combination may not be subjected to a vacuum, to heat above room temperature, or both. For example, the tubular member and conductive ink combination may be subjected to a room temperature environment where the combination is air dried.

In some example methods, the time period may correspond to a period of time it takes for the pretreated outer surface and the conductive ink to reach a desired percentage of crosslinking. In general, when two or more materials are to be bonded together, each material may include an amount of molecules that are available to be bonded with other molecules. A percentage of crosslinking may refer to the percentage of those available molecules that have been subjected to bonding. In some embodiments of the example method 1800, the desired percentage of crosslinking is 100%, meaning that an equilibrium state has been reached and no more bonding will occur between the molecules of the pretreated outer surface and the molecules of the conductive ink. Percentages less than 100% may be possible. Also, example time periods may be and/or within a range on the order of minutes (e.g., 5 minutes) or on the order of hours (e.g, about two to four hours). Also, where heat above room temperature is used in the curing phase, example temperatures of the heat inside the chamber may be in a range of about 180-300 degrees Fahrenheit (about 80-150 degrees Celsius). Other time periods and/or temperatures may be possible, and for some methods, the time period may depend on the temperature, or vice versa. At block 1810, the time period may expire, ending the curing phase and the example method 1800.

Figure 19:
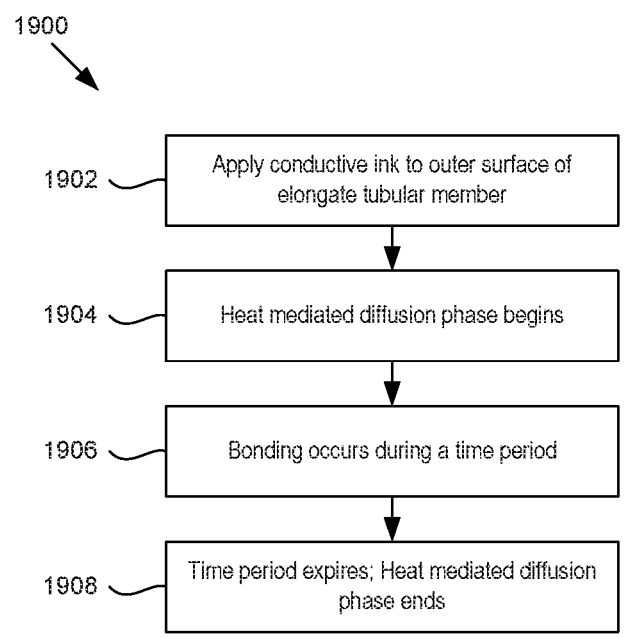
FIG. 19 is a flow chart of another example method of adhering conductive ink directly to an outer surface of a tubular member.

FIG. 19 is a flow chart of an example method 1900 of adhering a conductive ink portion to an elongate tubular member using mechanical bonding to bond a single conductive ink layer directly to the outer surface of the tubular member. At block 1902, the conductive ink may be applied to the outer surface of the tubular member. As in the method 1800 of FIG. 18, the conductive ink may be applied in various ways, such as pad printing, dipping, rolling, scraping, spraying, or electroplating, as non-limiting examples. However, unlike the method 1800 of FIG. 18, the outer surface may not be pretreated and the conductive ink may not include functional groups since mechanical bonding instead of covalent and/or electrostatic bonding is used to bond the conductive ink to the outer surface.

At block 1904, a heat mediated diffusion phase may begin. In general, during heat mediated diffusion, the tubular member and conductive ink combination may be placed inside a chamber, where it subjected to pressure and heat for a period of time. The combination of the pressure and the heat may cause the outer surface to melt and molecules of the outer surface and molecules of the conductive ink to mechanically bond with each other. Also, as with the example method 1800, the time period may correspond to a desired percentage of crosslinking between the outer surface and the conductive ink. For some embodiments of the example method 1900, the percentage may be 100%, although percentages less than 100% may be possible. Also, example time periods may be and/or within a range on the order of minutes (e.g., 5 minutes) or on the order of hours (e.g., about two to four hours). Also, example temperatures of the heat inside the chamber may be in a range of about 180-300 degrees Fahrenheit (about 80-150 degrees Celsius). In addition or alternatively, the temperature may be a percentage of a melting temperature of the materials of the outer surface and the conductive ink being diffused together. In some examples, the percentage may be within a percentage range of 25-75% of the melting temperature. Other time periods and/or temperatures may be possible, and for some methods the time period may depend on the temperature, or vice versa. In addition, an example amount of pressure applied to the tubular member and conductive ink combination may be greater than atmospheric pressure, such as in a range of about 1 Megapascal (MPa) to 15 MPa, although other amounts of pressure may be possible. At block 1908, the time period may expire, ending the heat mediated diffusion phase and the example method 1900.

Figure 20:
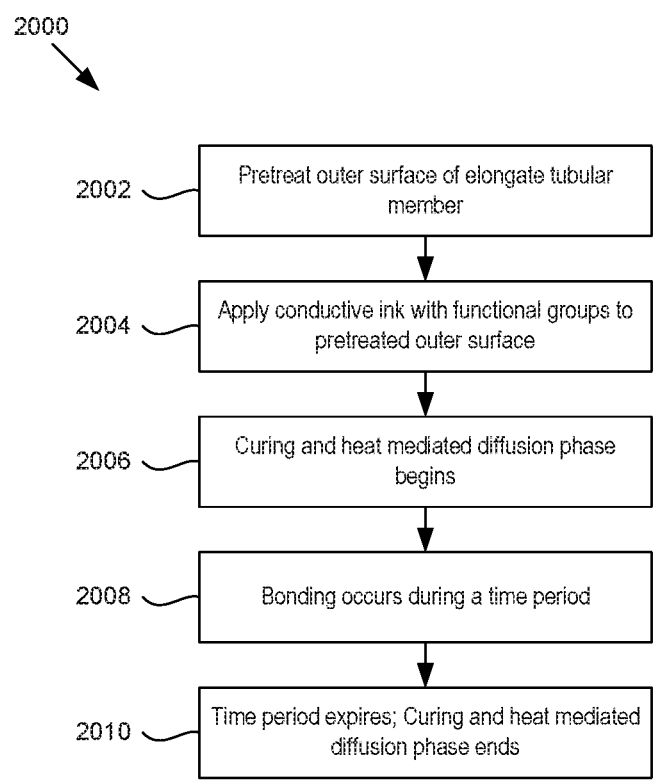
FIG. 20 is a flow chart of a third example method of adhering conductive ink directly to an outer surface of a tubular member.

FIG. 20 is a flow chart of an example method 2000 of adhering a conductive ink portion to an elongate tubular member using a combination of covalent and/or electrostatic bonding and mechanical bonding to bond the conductive ink portion directly to the outer surface of the tubular member. At block 2002, at least a portion of the outer surface of the tubular member where the conductive ink is to be applied may be pretreated. At block 2004, after the pretreatment is performed, conductive ink comprising functional groups may be applied to the pretreated outer surface. The pretreatment performed at block 2002 and the application of the conductive ink with functional groups to the pretreated outer surface at block 2004 may be performed in the same way or similar to the pretreatment and conductive ink application performed at blocks 1802 and 1804 of FIG. 18, respectively.

At block 2006, a combined curing and heat mediated diffusion phase may begin. During the combined curing and heat mediated diffusion phase, molecules of the outer surface and molecules of the conductive ink may bond together through a combination of covalent and/or electrostatic bonding and mechanical bonding. At block 2008, the tubular member and conductive ink combination may be placed inside a chamber and subjected to heat and pressure for a time period. The combination may optionally be subjected to a vacuum. During the combined curing and heat mediated diffusion phase, the outer surface may melt, and some molecules of the pretreated outer surface and the conductive ink may bond together through covalent and/or electrostatic bonding while other molecules may mechanically bond together due to the heat and pressure. The time period of the combined curing and heat mediated diffusion phase may correspond to a desired percentage of crosslinking, which may be 100% or less than 100%. Also, example time periods may be and/or within a range on the order of minutes (e.g., 5 minutes) or on the order of hours (e.g., about two to four hours), example temperatures of the heat inside the chamber may be in a range of about 180-300 degrees Fahrenheit (about 80-150 degrees Celsius) and/or correspond to a percentage of the melting temperature of the materials being diffused, and example amounts of pressure applied to the tubular member and conductive ink combination may be in a range of about 1 MPa to 15 MPa, although other time periods, temperatures, and/or amounts of pressure may be possible. At block 2008, the time period may expire, ending the combined curing and heat mediated diffusion phase and the example method 2000.

Figure 21:
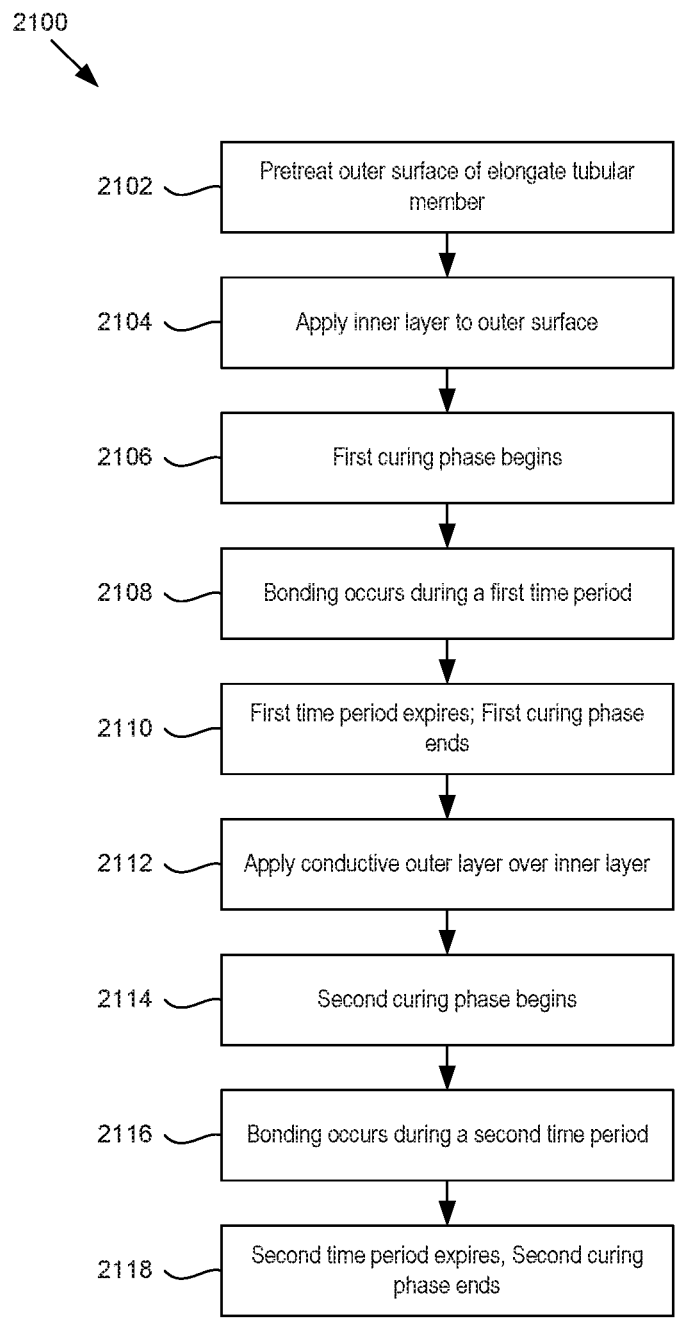
FIG. 21 is a flow chart of an example method of adhering conductive ink to an outer surface of a tubular member via a primer adhesive.

FIG. 21 is a flow chart of an example method 2100 of adhering a primer adhesive portion and a conductive ink portion to an outer surface of an elongate tubular member using covalent and/or electrostatic bonding. At block 2102, at least a portion of the outer surface of the tubular member where a primer adhesive is to be applied may be pretreated. The pretreatment performed at block 2102 may be the same or similar to the pretreatment performed at block 1802 and/or at block 2002 of the example methods 1800 and 2000 of FIGS. 18 and 20, respectively. At block 2004, after the pretreatment is performed, the primer adhesive may be applied to the pretreated outer surface to form a base coating or base layer. The primer adhesive may include functional groups (e.g., epoxide or epoxide resin) and/or other materials (e.g., cyanoacrylate, thiol, silane, triphenylphosphine, diaminodiphenylmethane, as previously described) to enhance bonding of the primer adhesive to the pretreated outer surface. In addition, the primer adhesive may be applied to the pretreated outer surface in various ways, including pad printing, dipping, rolling, scraping, or spraying, as non-limiting examples.

After the primer adhesive is applied to the pretreated outer surface at block 2104, a first curing phase of the example method 2100 may begin at block 2106. In the first curing phase, covalent and/or electrostatic bonds may form between the molecules of the primer adhesive and the molecules of the pretreated outer surface in order to directly adhere the primer adhesive to the outer surface to form the base layer.

At block 2108, during the first curing phase, a time period may elapse during which the covalent and/or electrostatic bonds may form. In some example methods, during the curing phase, the tubular member and primer adhesive combination may be placed inside a chamber, where it is subjected to a vacuum and heat above room temperature. In other example methods, the combination may not be subjected to a vacuum, heat, or both. For example, the combination may be subjected to a room temperature environment where the combination is air dried. The time period may correspond to a period of time it takes for the pretreated outer surface and the base ink to reach a desired percentage of crosslinking. In some embodiments of the example method 2100, the desired percentage may be 100%, while in other embodiments, the desired percentage may be less than 100%. An example percentage less than 100% may be in a range of about 10-75%, although percentages less than 100% and outside of this range may be possible. Also, example time periods may be and/or within a range on the order of minutes (e.g., 5 minutes) or on the order of hours (e.g., about two to four hours). Also, for methods that involve heat above room temperature, example temperatures of the heat inside the chamber may be in a range of about 180-300 degrees Fahrenheit (about 80-150 degrees Celsius). Other time periods and/or temperatures for the first curing phase may be possible, and for some methods, the time period may depend on the temperature, or vice versa. At block 2110, the first time period may expire, ending the first curing phase.

At block 2112, conductive ink may be applied to and/or over the primer adhesive. With the primer adhesive disposed in between the outer surface of the tubular member and the conductive ink, the primer adhesive may be considered the base layer or base coating, and the conductive ink may be considered the outer layer or conductive ink layer or conductive ink coating. Additionally, the conductive ink applied to the primer adhesive at block 2112 may or may not include functional groups. Also, similar to the application methods as previously described, the conductive ink may be applied to the primer adhesive in various ways, including pad printing, dipping, rolling, scraping, spraying, or electroplating, as non-limiting examples.

At block 2114, a second curing phase may begin. In the second curing phase, covalent and/or electrostatic bonds may form between the molecules of the base and conductive ink layers. Additionally, for embodiments where 100% crosslinking between the pretreated outer surface of the tubular member and the primer adhesive was not achieved, additional bonding between the outer surface and the primer adhesive may occur.

At block 2116, during the second curing phase, a second time period may elapse during which the covalent and/or electrostatic bonding may occur. In some example methods, the tubular member, base layer, and conductive ink layer combination may be placed inside a chamber, where it is subjected to a vacuum and heat above room temperature. In other example methods, the combination may not be subjected to a vacuum, heat, or both. For example, the combination may be subjected to room temperature. The second time period may correspond to a desired percentage of crosslinking among the outer surface, the primer adhesive, and the conductive ink. An example desired percentage may be 100%, although embodiments where less than 100% crosslinking is achieved during the second curing phase may be possible. Also, example time periods may be and/or within a range on the order of minutes (e.g., 5 minutes) or on the order of hours (e.g., about two to four hours), and example temperatures of the heat inside the chamber may be in a range of about 180-300 degrees Fahrenheit (about 80-150 degrees Celsius). Other time periods and/or temperatures above room temperature may be possible, and for some methods, the time period may depend on the temperature, or vice versa. At block 2118, the second time period may expire, ending the second curing phase and the example method 2100.

Figure 22:
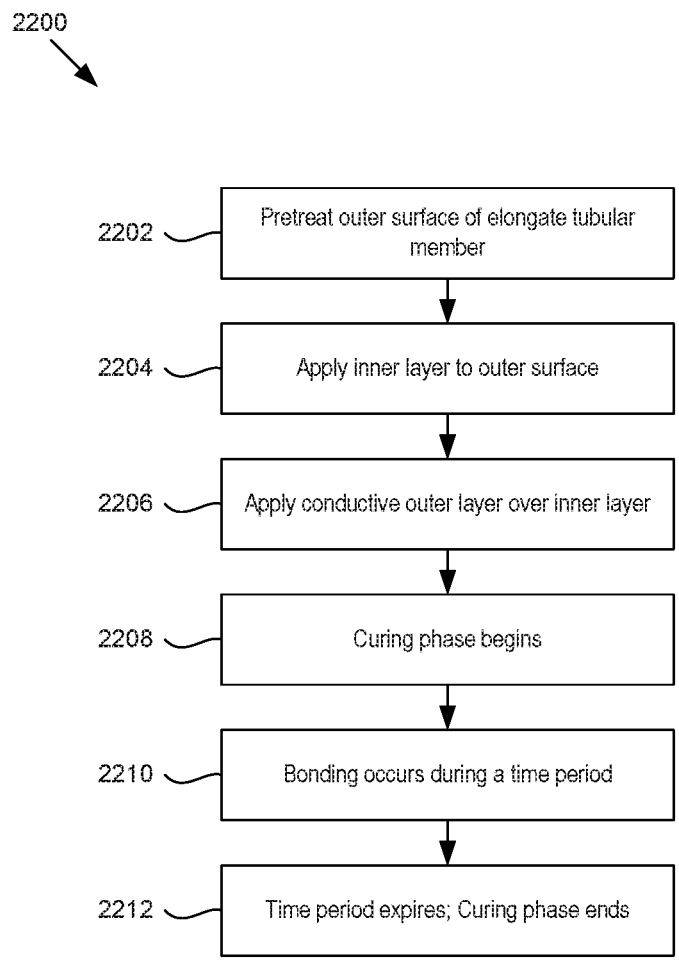
FIG. 22 is a flow chart of another example method of adhering conductive ink to an outer surface of a tubular member via a primer adhesive.

FIG. 22 is a flow chart of another example method 2200 of adhering a primer adhesive portion and a conductive ink portion to an outer surface of an elongate tubular member using covalent and/or electrostatic bonding. At block 2202, at least a portion of the outer surface of the tubular member where the primer adhesive is to be applied may be pretreated. The pretreatment performed at block 2202 may be the same or similar to the pretreatment performed at blocks 1802, 2002, and/or 2102 of the example methods 1800, 2000, 2100 of FIGS. 18, 20, 21 respectively. At block 2204, the primer adhesive may be applied to the pretreated outer surface, such as using pad printing, dipping, rolling, scraping, or spraying as previously described. At block 2206, a conductive ink may be applied to and/or over the primer adhesive. The conductive ink that is applied to the primer adhesive at block 2206 may or may not include functional groups. Application of the conductive ink may be applied at block 2206 without first performing a first curing phase separately for the primer adhesive. Similar to the example method 2100, the conductive ink may be applied to the primer adhesive using pad printing, dipping, rolling, scraping, spraying, or electroplating, as non-limiting examples.

After the primer adhesive is applied to the pretreated outer surface and the conductive ink is applied to the primer adhesive, a curing phase may begin at block 2208. In the curing phase, covalent and/or electrostatic bonds may form between molecules of the primer adhesive and the pretreated outer surface to bond the primer adhesive directly to the outer surface. Additionally, covalent and/or electrostatic bonds may form between molecules of the primer adhesive and the conductive ink to bond the primer adhesive with the conductive ink.

At block 2210, during the curing phase, a time period may elapse during which the covalent and/or electrostatic bonds may form. For some example methods, the elongate tubular member, primer adhesive, and conductive ink combination may be placed inside a chamber, where it is subjected to a vacuum and heat. In other example methods, the combination may not be subjected to a vacuum, heat, or both. For example, the combination may be subjected to room temperature, where it is air dried. The time period may correspond to a period of time it takes for the pretreated outer surface, primer adhesive, and the conductive ink to reach a desired percentage of crosslinking. In some embodiments of the example method 2200, the desired percentage may be 100%, while in other embodiments, the desired percentage may be less than 100%. Also, example time periods may be and/or within a range on the order of minutes (e.g., 5 minutes) or on the order of hours (e.g., about two to four hours), and example temperatures of the heat inside the chamber may be in a range of about 180-300 degrees Fahrenheit (about 80-150 degrees Celsius). Other time periods and/or temperatures for the curing phase may be possible, and for some methods, the time period may depend on the temperature, or vice versa. At block 2112, the time period may expire, ending the curing phase and the example method 2200.

Figure 23:
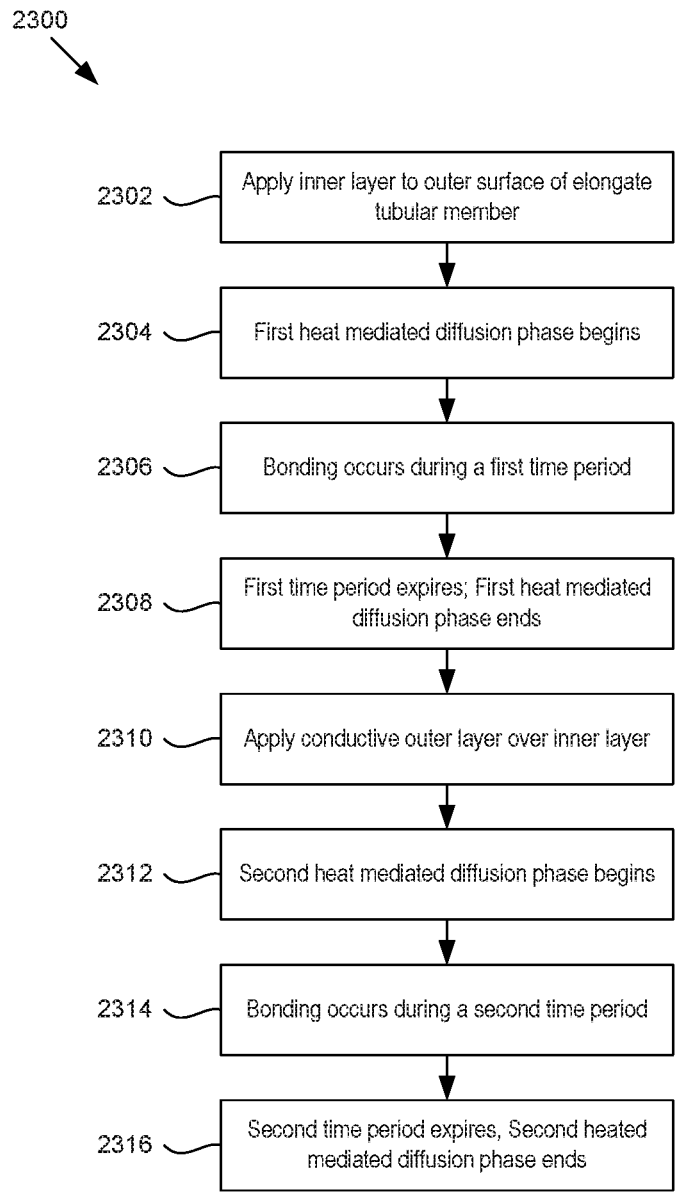
FIG. 23 is a flow chart of a third example method of adhering conductive ink to an outer surface of a tubular member via a primer adhesive.

FIG. 23 is a flow chart of an example method 2300 of adhering a primer adhesive portion and a conductive ink portion using mechanical bonding. At block 2302, the primer adhesive may be applied to the outer surface of the tubular member. As with the example methods 2100 and 2200, the primer adhesive may be applied in various ways, such as pad printing, dipping, rolling, scraping, or spraying, as non-limiting examples.

At block 2304, after the primer adhesive is applied to the outer surface, a first heat mediated diffusion phase may begin. During the first heat mediated diffusion phase, a combination of pressure and heat may cause the outer surface to melt and molecules of the outer surface and the molecules of the primer adhesive to mechanically bond with each other. At block 2306, during the first heat mediated diffusion phase, the tubular member and primer adhesive combination may be placed in a chamber, where the combination is subjected to pressure and heat for a first time period, such as a predetermined time period, which may correspond to a desired percent crosslinking between the outer surface and the primer adhesive. In some embodiments of the example method 2300, the desired percentage may be 100%, while in other embodiments, the desired percentage may be less than 100%. An example percentage less than 100% may be in a range of about 10-75%, although percentages less than 100% and outside of this range may be possible. Also, example time periods may be and/or within a range on the order of minutes (e.g., 5 minutes) or on the order of hours (e.g., about two to four hours), and example temperatures of the heat inside the chamber may be in a range of about 180-300 degrees Fahrenheit (about 80-150 degrees Celsius) and/or correspond to a percentage of the melting temperature of the materials being diffused. Other time periods and/or temperatures for the first heat diffusion phase may be possible, and for some methods, the time period may depend on the temperature, or vice versa. Additionally, an example amount of pressure applied during the first time period may be in a range of about 1 MPa to 15 MPa, although other amounts of pressure may be possible. At block 2308, the first time period may expire, ending the first heat mediated diffusion phase.

At block 2310, conductive ink may be applied to and/or over the base layer. The conductive ink applied to the primer adhesive at block 2310 may or may not include functional groups. Also, similar to the application methods as previously described, the conductive ink may be applied to the primer adhesive in various ways, including pad printing, dipping, rolling, scraping, spraying, or electroplating, as non-limiting examples.

At block 2312, a second heat mediated diffusion phase may begin. During the second heat mediated diffusion phase, a combination of pressure and heat may cause the outer surface of the primer adhesive to melt and molecules of the primer adhesive outer surface and molecules of the conductive ink to mechanically bond with each other. At block 2314, during the second heat mediated diffusion phase, the tubular member, primer adhesive, and conductive ink combination may be placed inside a chamber, where it is subjected to a pressure and heat for a second time period, such as a predetermined second time period, which may correspond to a desired percentage of crosslinking between the outer surface of the base layer and the conductive ink layer. An example desired percentage may be 100%, although embodiments where less than 100% crosslinking is achieved during the second curing phase may be possible. Additionally, where 100% crosslinking is not achieved between the outer surface of the tubular member and the primer adhesive, further mechanical bonding between the outer surface of the tubular member and the primer adhesive may occur during the second heat mediated diffusion phase. Also, example time periods may be and/or within a range on the order of minutes (e.g., 5 minutes) or on the order of hours (e.g., about two to four hours), example temperatures of the heat inside the chamber may be in a range of about 180-300 degrees Fahrenheit (about 80-150 degrees Celsius) and/or correspond to a percentage of the melting temperature of the materials being diffused, and example amounts of pressure may be in a range of about 1 MPa to 15 MPa, although other time periods, temperatures, and/or amounts of pressure may be possible. At block 2316, the second time period may expire, ending the second heat mediated diffusion phase and the example method 2300.

Figure 24:
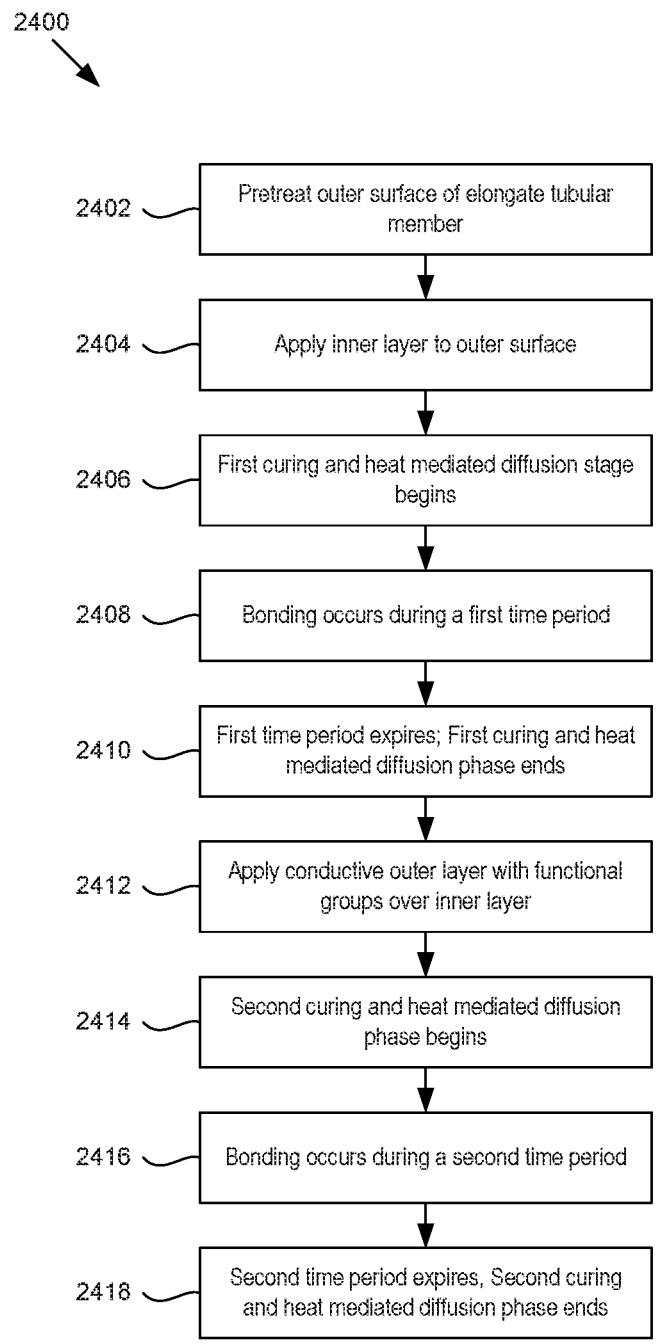
FIG. 24 is a flow chart of a fourth example method of adhering conductive ink to an outer surface of a tubular member via a primer adhesive.

FIG. 24 is a flow chart of an example method 2400 of adhering a primer adhesive portion and a conductive ink portion to an elongate tubular member using a combination of covalent and/or electrostatic bonding and mechanical bonding. At block 2402, at least a portion of the outer surface of the tubular member where the primer adhesive is to be applied may be pretreated. The pretreatment performed at block 2402 may be the same or similar to the pretreatment performed at blocks 1802, 2002, 2102, 2202 of the example methods 1800, 2000, 2100, 2200 of FIGS. 18, 20, 21, 22 respectively. At block 2204, the primer adhesive may be applied to the pretreated outer surface, such as using pad printing, dipping, rolling, scraping, or spraying as previously described.

At block 2406, a first combined curing and head mediated diffusion phase may begin. During the first combined curing and heat mediated diffusion phase, molecules of the outer surface and molecules of the primer adhesive may bond together through a combination of covalent and/or electrostatic bonding and mechanical bonding. At block 2408, the tubular member and primer adhesive combination may be placed inside a chamber and subjected to a heat above room temperature, pressure, and optionally a vacuum for a first time period. During the first combined curing and head mediated diffusion phase, the outer surface may melt, and some molecules of the pretreated outer surface and the primer adhesive may bond together through covalent covalent and/or electrostatic bonding while other molecules may mechanically bond together due to the heat and pressure. Additionally, the first time period may correspond to a desired percentage of crosslinking, which may be 100% or less than 100%. An example percentage less than 100% may be in a range of about 10-75%, although percentages less than 100% and outside of this range may be possible. Also, example time periods may be and/or within a range on the order of minutes (e.g., 5 minutes) or on the order of hours (e.g., about two to four hours), example temperatures of the heat inside the chamber may be in a range of about 180-300 degrees Fahrenheit (about 80-150 degrees Celsius) and/or correspond to a percentage of the melting temperature of the materials being diffused, and example amounts of pressure applied to the tubular member and primer adhesive combination may be in a range of about 1 MPa to 15 MPa, although other time periods, temperatures, and/or amounts of pressure may be possible. At block 2410, the first time period may expire, ending the first combined curing and heat mediated diffusion phase.

At block 2412, conductive ink may be applied to and/or over the base layer. The conductive ink applied to the base layer at block 2412 may or may not include functional groups. Also, similar to the application methods as previously described, the conductive ink may be applied to the base layer in various ways, including pad printing, dipping, rolling, scraping, spraying, or electroplating, as non-limiting examples.

At block 2414, a second combined curing and heat mediated diffusion phase may begin. During the second combined curing and heat mediated diffusion phase, molecules of the outer surface of the primer adhesive and molecules of the conductive ink may bond together through a combination of covalent and/or electrostatic bonding and mechanical bonding. Also, if less than 100% crosslinking occurred during the first combined curing and heat mediated diffusion phase, then additional bonding between molecules of the outer surface of the tubular member and the primer adhesive may occur during the second combined curing and heat mediated diffusion phase.

At block 2416, the tubular member, primer adhesive, and conductive ink combination may be placed inside a chamber and subjected to a heat, pressure, and optionally a vacuum for a second time period. During the second combined curing and heat mediated diffusion phase, the outer surface of the primer adhesive may melt, and some molecules of the primer adhesive and the conductive ink may bond together through covalent and/or electrostatic bonding while other molecules of the primer adhesive and the conductive ink may mechanically bond together due to the heat and pressure. Also, as mentioned, if less than 100% crosslinking between the outer surface of the tubular member and the primer adhesive occurred during the first combined curing and heated mediated diffusion stage, then further bonding between molecules of the outer surface of the tubular member and the primer adhesive may occur during the second time period. The second time period may correspond to a desired percentage of crosslinking, which may be 100%, although a desired percentage of crosslinking less than 100% may be possible. Also, example time periods may be and/or within a range on the order of minutes (e.g., 5 minutes) or on the order of hours (e.g., about two to four hours), example temperatures of the heat inside the chamber may be in a range of about 180-300 degrees Fahrenheit (about 80-150 degrees Celsius) and/or correspond to a percentage of the melting temperature of the materials being diffused, and example amounts of pressure applied to the tubular member and primer adhesive combination may be in a range of about 1 MPa to 15 MPa, although other time periods, temperatures, and/or amounts of pressure may be possible. At block 2418, the second time period may expire, ending the second combined curing and heat mediated diffusion phase and the example method 2400.

Methods of adhering conductive ink to an elongate tubular member other than those described with reference to FIGS. 18-24 may be possible, including those that utilize one or more of: including functional groups in the conductive ink, pretreating the outer surface of the tubular member 102, applying a primer adhesive to the outer surface of the tubular member 102 before applying the conductive ink, or mechanically bonding the conductive ink and/or the primer adhesive to the outer surface of the tubular member. For example, mechanical bonding through heat mediated diffusion may be used to adhere the primer adhesive to the outer surface of the tubular member, and covalent and/or electrostatic bonding may utilized to adhere the conductive ink layer to the primer adhesive, or vice versa. Still other methods may involve applying more than one primer adhesive layer and/or more than one conductive ink layer (or applying the primer adhesive and/or the conductive ink each in multiple steps). Various other methods may be possible.

Additionally, application of conductive ink to bipolar endoscopic medical devices, and bipolar sphincterotomes in particular, is merely one application for which the methods described with reference to FIGS. 18-24 can be used. More generally, the methods can be applied in any situation where adhering or attaching a polymer-based ink or other similar coating, with or without conductive particles, to a hydrophobic, adhesion-resistant, and/or non-stick surface of a structure is desired, especially those structures that bend or curl during their use.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A bipolar sphincterotome comprising:
a cutting edge;
an elongate tubular member comprising an adhesion-resistant outer surface, the elongate tubular member comprising an opening and an anchor point distal the opening, wherein the cutting edge extends from the opening to the anchor point;
a primer adhesive directly adhered to the adhesion-resistant outer surface; and
a conductive coating directly adhered to the primer adhesive,
wherein the primer adhesive and the conductive coating longitudinally extend alongside at least a portion of the cutting edge and proximally past the opening.

2. The bipolar sphincterotome of claim 1, wherein the primer adhesive comprises at least one of: epoxy resin, cyanacrylate, thiol, silane, triphenylphosphine, diaminodiphenylmethane.

3. The bipolar sphincterotome of claim 1, wherein the outer surface comprises at least one of a fluoropolymer material or a polyolefin material.

4. The bipolar sphincterotome of claim 1, wherein the conductive coating comprises elongate conductive particles.

5. The bipolar sphincterotome of claim 1, wherein the primer adhesive and the conductive coating longitudinally extend over a distal portion of the elongate tubular member that is configured to curl when a cutting wire of the bipolar sphincterotomes is pulled taut.

6. The bipolar sphincterotome of claim 1, wherein the primer adhesive does not include any conductive particles.

7. The bipolar sphincterotome of claim 1, wherein the conductive coating comprises functional groups comprising at least one of: epoxide functional groups, amine functional groups, ketone functional groups, or alcohol functional groups.

* * * * *